United States Patent [19]

Kung

[11] Patent Number: 5,690,906
[45] Date of Patent: Nov. 25, 1997

[54] DOPAMINE D-3 AND SEROTONIN ($5-HT_{1A}$) RECEPTOR LIGANDS AND IMAGING AGENTS

[75] Inventor: Hank F. Kung, Wynnewood, Pa.

[73] Assignee: The Trustees of the University of Pennsylvania, Philadelphia, Pa.

[21] Appl. No.: 445,161

[22] Filed: May 19, 1995

Related U.S. Application Data

[63] Continuation of Ser. No. 40,497, Mar. 31, 1993, abandoned.

[51] Int. Cl.$^6$ .................. A61K 51/04; C07D 221/00; C07D 311/00; C07D 335/04
[52] U.S. Cl. .................. 424/1.85; 544/32; 544/101; 544/34; 546/80; 546/89; 546/110; 549/23; 549/404; 564/307; 564/308
[58] Field of Search .................. 424/1.85; 544/32, 544/34, 101; 546/80, 89, 110; 549/23, 404; 564/307, 308

[56] References Cited

U.S. PATENT DOCUMENTS

| | | | |
|---|---|---|---|
| 4,163,063 | 7/1979 | Cannon et al. | 424/330 |
| 4,298,591 | 11/1981 | O'Brien, Jr. et al. | 424/1 |
| 4,420,480 | 12/1983 | Jones | 424/248.4 |
| 4,448,990 | 5/1984 | Bach et al. | 564/167 |
| 4,500,545 | 2/1985 | Bach et al. | 514/619 |
| 4,556,676 | 12/1985 | Welch, Jr. et al. | 514/554 |
| 4,564,628 | 1/1986 | Horn | 514/438 |
| 4,657,925 | 4/1987 | Horn | 514/438 |
| 4,722,933 | 2/1988 | Horn | 514/438 |
| 4,845,221 | 7/1989 | Stack et al. | 544/295 |
| 4,876,284 | 10/1989 | Arvidsson et al. | 514/657 |
| 4,882,352 | 11/1989 | Horn | 514/438 |
| 4,885,308 | 12/1989 | Horn | 514/438 |
| 4,920,227 | 4/1990 | Pelletier et al. | 546/133 |
| 4,931,270 | 6/1990 | Horn et al. | 424/1.1 |
| 4,943,428 | 7/1990 | Lucot et al. | 424/10 |
| 4,996,226 | 2/1991 | Horn | 514/438 |
| 5,071,875 | 12/1991 | Horn et al. | 514/613 |
| 5,086,074 | 2/1992 | DeBernardis et al. | 514/649 |
| 5,128,362 | 7/1992 | DeBernardis et al. | 514/408 |
| 5,140,040 | 8/1992 | DeBernardis et al. | 514/422 |
| 5,286,753 | 2/1994 | Schaus et al. | 514/657 |
| 5,298,513 | 3/1994 | Scohe et al. | 514/319 |

FOREIGN PATENT DOCUMENTS

| | | |
|---|---|---|
| A-0 064 964 A1 | 11/1982 | European Pat. Off. . |
| 0 498 590 A1 | 12/1992 | European Pat. Off. . |

OTHER PUBLICATIONS

Foulon et al., "Synthesis of (R,S)-2'-trans-7-Hydroxy-2-[N-n-propyl-N-(3'-iodo-2'-propenyl)-amino]tetralin (trans-7-OH-PIPAT):A New D3 Dop-amine Receptor Ligand", J. Med. Chem. 36:1499-1500 (1993).

Kung et al., "In Vitro Binding of a Novel Dopamine D3 Receptor Ligand", Eur. J. Pharm., 235:165-166 (1993).

Lin et al., "Centrally Acting Serotonergic Agents . . . ", J. Med. Chem., 36:671-682 (1993).

Beart et al., "Radioreceptor Binding Reveals the Potencies of N,N-Disubstituted 2-Aminotetralins as $D_2$ Dopamine Agonists," Naunyn-Schmiedeberg's Arch. Pharmacol. 336:487-493 (1987).

Foulon et al., "Synthesis of (R,S)-2'-Trans-7-Hydroxy-2-[N-n-propyl-N-(3'-iodo-2'-propenyl)-amino]tetralin (trans-7-OH-PIPAT): A New D3 Dopamine Receptor Ligand", Journal of Medicinal Chemistry 36:1499-1500 (1993).

(List continued on next page.)

*Primary Examiner*—John Kight
*Assistant Examiner*—Lara E. Chapman
*Attorney, Agent, or Firm*—Woodcock Washburn Kurtz Mackiewicz & Norris LLP

[57] ABSTRACT

Tetralin derivatives, such as 7-hydroxy-2-(N-n-propyl-N-3'-iodo-2'-propenyl)-amino]tetralin and 8-hydroxy-2-(N-n-propyl-N-3'-iodo-2'-propenyl)amino-tetralin, are disclosed which have affinity and specificity for dopamine D-3 and/or serotonin $5-HT_{1A}$ receptors.

41 Claims, 2 Drawing Sheets

OTHER PUBLICATIONS

Johansson, et al., "C3-Methylated 5-Hydroxy-2-(dipropylamino)tetralins: Conformational and Steric Parameters of Importance for Central Dopamine Receptor Activation", *J. Med Chem.* 30: 1135–1144 (1987).

Karlsson et al., "Improved Preparation, Chromatographic Separation and X-Ray Crystallographic Determination of the Absolute Configuration of the Enantiomers of 8-Hydroxy-2-(dipropylamino)tetralin (8-OH DPAT)", *Acta. Chim. Scan* B42:231–236 (1988).

Kung, M-P et al., "In Vitro Binding of a Novel Dopamine $D_3$ Receptor Ligand: [$^{125}$I]trans-7-OH-PIPAT-A", *European Journal of Pharmacology* 235:165–166 (1993).

Kung M.-P et al., "The Characterization of IBF as a New Selective Dopamine D-2 Receptor Imaging Agent", *J. Nucl. Med.* 31:648–654 (1990).

Lévesque et al., "Identification, Characterization and Localization of the Dopamine D3 Receptor in Rat Brain Using 7-[$^3$H]hydroxy-N,N-di-n-propyl-2-aminotetralin," *Proc. Natl. Acad. Sci. USA* 89:8155–8159 (1992).

McDermed et al., "Synthesis and Dopaminergic Activity of (±)-, (+)-, and (-)-2-Dipropylamino-5-hydroxy-1,2,3, 4-tetrahydronaphthalene", *J. Med. Chem.* 19:547–549 (1976).

McDermed et al., "Synthesis and Pharmacology of Some 2-Aminotetralins. Dopamine Receptor Agonists", *J. Med. Chem.* 18:362–367 (1975).

Mellin et al., "Central Dopaminergic and 5-Hydroxytryptaminergic Effects of C3-Methylated Derivatives of 8-Hydroxy-2-(di-n-propylamino) tetralin", *J. Med. Chem.* 31:1130–1140 (1988).

Mulder et al., "Further in vitro and in vivo Studies with the Putative Presynaptic Dopamine Agonist N,N-Dipropyl-7-Hydroxy-2-Aminotetralin," *Naunyn–Schmiedenberg's Arch. Pharmacol.* 336:494–501 (1987).

Sokoloff, P., et al., "Molecular Cloning and Characterization of a Novel Dopamine Receptor ($D_3$) as a Target for Neuroleptics," *Nature* 347:146–151 (1990).

Sokoloff, P., et al., "The Third Dopamine Receptor ($D_3$) as a Novel Target for Antipsychotics," *Biochemical Pharmacology* 43:659–666 (1992).

Wickström, H., "Centrally Acting Dopamine D2 Receptor Ligands: Agonists," *Prog. in Med. Chem.* 29:185–216 (1992).

Wise et al., "6- and 8-Hydroxy-3, 4-Dihydro-3-(Dipropylamino)-2H-1-Benzopyrans. Dopamine Agonists with Autoreceptor Selectivity", *J. Med. Chem.* 31: 688–691 (1988).

Arvidsson et al., "8-Hydroxy-2-(di-n- propylamino) tetralin, a New Centrally Acting 5-Hydroxytryptamine Receptor Agonist", *J. Med. Chem.* 24: 921–923 (1981).

Arvidsson et al., "(+)-cis-8-Hydroxy-1-methyl-2-(di-n-propylamino)tetralin: A Potent and Highly Stereoselective 5-Hydroxytryptamine Receptor Agonist", *J. Med. Chem.* 30:2105–2109 (1987).

Asselin et al., "Drug Design via Pharmacophore Identification. Dopaminergic Activity of 3H-Benz[e]indol-8-amines and Their Mode of Interaction with the Dopamine Receptor", *J. Med. Chem.* 29:648–654 (1986).

Bakthavachalam et al., "Fluorescent Probes for Dopamine Receptors: Synthesis and Characterization of Fluorescein and 7-Nitrobenz-2-oxa-1, 3-diazol-4-yl Conjugates of D-1 and D-2 Receptor Ligands", *J. Med. Chem.* 34:3235–3241 (1991).

Cannon et al., "1-(Aminomethyl)-6, 7-dihydroxytetralin Derivatives: Synthesis and Assessment of Dopamine-Like Effects", *J. Med. Chem.* 26:813–816 (1983).

Cannon et al., "Comparison of Biological Effects of N-Alkylated Congeners of β-Phenethylamine Derived from 2-Aminotetralin, 2-Aminoindan, and 6-Aminobenzocycloheptene", *J. Med. Chem.* 23:745–749 (1980).

Cannon et al., "Introduction of a Putative Dopaminergic Prodrug Moiety into a 6,7-Substitution Pattern Characteristic of Certain 2-Aminotetralin Dopaminergic Agonists", *J. Med. Chem.* 32:2210–2214 (1989).

DeWald et al., "Synthesis and Dopamine Agonist Properties of (±)-trans-3,4,4a,10b-Tetrahydro-4-propyl-2H, 5H-[1] benzopyrano[4,3-b]-1,4-oxazin-9-ol and Its Enantiomers", *J. Med. Chem.* 33:445–450 (1990).

Duncan et al., "Metabolism of Aminotetralin Analogues in vivo and by Rat Hepatocytes", *Biochemical Society Transact.:* 1200–1201 (1990).

Grol et al., "5-Oxygenated N-Alkyl- and N,N-Dialkyl-2-amino-1-methyltetralins. Effects of Structure and Stereochemistry on Dopamine-$D_2$-Receptor Affinity", *J. Pharm. Pharmacol.* 43:481–485 (1991).

Hall et al., "Synthesis of Some [N-(2-Haloalkyl)amino] tetralin Derivatives as Potential Irreversible Labels for Bovine Anterior Pituitary $D_2$ Dopamine Receptors" *J. Med. Chem.* 30:1879–1887 (1987).

Horn et al., "6,7-Dihydroxy-3-chromanamine: Synthesis and Pharmacological Activity of an Oxygen Isostere of the Dopamine Agonist 6,7-Dihydroxy-2-aminotetralin", *J. Med. Chem.* 27: 1340–1343 (1984).

Johansson et al., "C1- and C3-Methyl-Substituted Derivatives of 7-Hydroxy-2-(di-n-propylamino)tetralin: Activities at Central Dopamine Receptors", *J. Med. Chem.* 30: 1827–1837 (1987).

Johansson et al., "Dopaminergic 2-Aminotetralins: Affinities for Dopamine $D_2$-Receptors, Molecular Structures, and Conformational Preferences", *Molecular Pharmacology* 30:258–269 (1986).

Johansson et al., "Novel Dopamine Receptor Agonists and Antagonists with Preferential Action on Autoreceptors", *J. Med. Chem.* 28:1049–1053 (1985).

Johansson et al., "Resolved cis- and trans-2-Amino-5-methyoxy-1-methyltetralins: Central Dopamine Receptor Agonists and Antagonists", *J. Med. Chem.* 30:602–611 (1987).

Johansson et al., "Syntheses of 5-, 7-, and 8-Methoxy-3-methyl-2-tetralone", *J. Org. Chem.* 51: 5252–5258 (1986).

Johansson et al., "Synthesis and Pharmacology of the Enantiomers of cis-7-Hydroxy-3-methyl-2-(dipropylamino)tetralin", *J. Med. Chem.* 33:2925–2929 (1990).

Jones et al., "Synthesis of 4-Substituted 2H-Naphth[1,2-b]-1,4-oxazines, a New Class of Dopamine Agonists", *J. Med. Chem.* 27:1607–1613 (1984).

Langlois and Gaudy, "A New Synthesis of 8-Hydroxy-2-DI-n-Propylamino-Tetralin (8-OH-D-PAT)", *Synthetic Communications* 22:1723–1734 (1992).

Lin et al., "Centrally Acting Serotonergic Agents. Synthesis and Structure–Activity Relationships of C–1– or C–3–Substituted Derivatives of 8–Hydroxy–2–(di–n–propylamino)tetralin", *J. Med. Chem.* 36:671–682 (1993).

Liu et al., "(R)– and (S)–5,6,7,8–Tetrahydro–1–hydroxy–N, N–dipropyl–9H–benzocyclohepten–8–ylamine. Stereoselective Interactions with 5–HT$_{1A}$ Receptors in the Brain", *J. Med. Chem.* 32:2311–2318 (1989).

Martin et al., "Pharmacologic Profile of a Novel Potent Direct–Acting Dopamine Agonist, (+)–4–Propyl–9–Hydroxynaphthoxazine [(+)–PHNO]", *J. Pharmacology and Experimental Therapeutics* 230:569–576 (1989).

Neumeyer et al., "R and S Enantiomers of 11–Hydroxy– and 10,11–Dihydroxy–N–allylnoraporphine: Synthesis and Affinity for Dopamine Receptors in Rat Brain Tissue", *J. Med. Chem.* 34:24–28 (1991).

Seiler et al., "Further Characterization of Structural Requirements for Agonists at the Striatal Dopamine D–1 Receptor", *Molecular Pharmacology* 22:281–289 (1982).

Sibley and Monsma, "Molecular Biology of Dopamine Receptors", *TIPS* 13: 61–68 (1992).

Wickström et al., "Resolved Monophenolic 2–Aminotetralins and 1,2,3,4,4a,5,6,10b–Octahydrobenzo[f]quinolines: Structural and Stereochemical Considerations for Cetnrally Acting Pre– and Postsynaptic Dopamine–Receptor Agonists", *J. Med. Chem.* 28:215–225 (1985).

Zorn and Rosen, "Molecular Cloning and Characterization of a Novel Dopamine Receptor (D$_3$) as a Target of Neuroleptics: Condensation of the Research", *Chemtracts–Organic Chemistry* 4:64–67 (1991).

DOPAMINE D-3 AND SEROTONIN (5-HT$_{1A}$) RECEPTOR LIGANDS AND IMAGING AGENTS

This is a continuation of application Ser. No. 08/040,497, filed Mar. 31, 1993, now abandoned.

GOVERNMENT SUPPORT

The work reported herein was supported at least in part by NIH NS-24538 and MH-48125.

FIELD OF THE INVENTION

This invention relates to derivatives of tetralin which are selective for dopamine D-3 or serotonin (5-HT$_{1A}$) receptors, to methods of preparing such ligands, to methods of utilizing them as imaging agents, and to novel compounds useful as intermediates in the preparation of such ligands.

BACKGROUND OF THE INVENTION

Neural transmitters are chemicals in the brain that are used to send messages from one brain cell to another. Neurotransmitters bind to special receptor proteins in the membrane of nerve cells, like a key in a lock, triggering a chemical reaction within the cell. Dopamine is one form of neural transmitter; serotonin is another.

In the late seventies, two classes of dopamine receptors, D1 and D2, were reported based on their different pharmacological, biochemical and physiological properties. However, subsequent studies showed the limit of this model. The existence of additional subtypes of dopamine receptors was proposed. Recently, the progress in molecular biology has revealed at least five genes coding for at least six different dopamine receptors: D1, D2$_S$, D2$_L$, D3, D4 and D5. These six subtypes can be categorized as D1-like (D1 and D5) or D2-like (D2$_S$, D2$_L$, D3 and D4) according to their pharmacological profile.

Imbalances in dopamine production and use have been implicated in a variety of mental disorders. The ability of several conventional and "atypical" neuroleptics to bind D3 receptors with as high affinity as D2 receptors has been shown. (Sokoloff, P., et al., "Molecular cloning and characterization of a novel dopamine receptor (D$_3$) as a target of neuroleptics," *Nature* 1990, 347, 146–151; Sokoloff, P., et al., "The third dopamine receptor (D3) as a novel target for antipsychotics," *Biochemical Pharmacology* 1992, 43, 659–666) These results have led to the hypothesis that the treatment of psychoses could be mediated by the action of neuroleptics on the D3 and D4 receptors. Therefore, the development of D3 specific ligands may lead to new drugs with more selective pharmacological profiles.

It is not only desirable to find new compounds selective to D3 receptors for possible pharmacological activity; such specific ligands are desired as they may be useful for monitoring the effectiveness of drugs and substances which affect brain chemistry. For instance, it is highly desirable to be able to gauge the biochemical effects of drugs administered for blocking the patient's dopamine receptors. If too little of the drug is administered, the desired blockade does not occur, and if too much of the drug is administered, there can be severe side effects.

New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs is based upon the comparisons made. For these methods to be useful, however, a ligand which has high affinity and specificity for the desired receptor is required.

A number of tetralins and related ergoline derivatives have been reported as centrally acting D2 dopamine receptor agonists. (Wickstrom, H., "Centrally acting dopamine D2 receptor ligands: agonists," *Prog. in Med. Chem.* 1992, 29, 185–216) Among the compounds that have been tested are 5-hydroxy-2-N,N-n-dipropylaminotetralin (5-OH-DPAT), 7-OH-DPAT and 8-OH-DPAT. 7-OH-DPAT, previously described as a presynaptic dopamine agonist (Mulder, T. B. A., et al., "Further in vitro and in vivo studies with the putative presynaptic dopamine agonist N,N-dipropyl-7-hydroxy-2-aminotetralin," *Naunyn-Schmiedenberg's Arch. Pharmacol.*, 1987, 336, 494–501; Beart, P.M., et al, "Radioreceptor binding reveals the potency of N,N-disubstituted-2-aminotetralins as D2 dopamine agonists," *Naunyn-Schmiedeberg's Arch. Pharmacol.* 1987, 336, 487–493) has been recently reported as a specific and selective ligand for the D3 receptors. (Levesque, D., et al., "Identification, characterization and localization of the dopamine D3 receptor in rat brain using 7-[$^3$H]-hydroxy-N,N-di-n-propyl-2-aminotetralin," *Proc. Natl. Acad. Sci. USA* 1992, 89, 8155–8159)

There remains, however, a clear need for potent and selective ligands for the D3 receptor subtypes which ligands may not only have pharmacological activity but which can also be labelled with high specific activity to aid the progress of understanding the pharmacological function and regulation of the receptor subtype in its native state.

Serotonin is a neural transmitter that has been linked with depression and with other psychiatric disorders such as eating disorders, alcoholism, pain, anxiety and obsessive-compulsive behavior. One of the serotonin receptor subtypes, 5-HT$_{1A}$, plays an important function as the somatodendretic autoreceptor in the dorsal raphe nucleus and as a postsynaptic receptor for 5-HT in terminal field areas. The compound 8-hydroxy-2-(di-n-propylamino)tetralin (8-OH-DPAT) has been disclosed as a potent and selective serotonin (5-HT$_{1A}$) receptor. (See, e.g., Mellin, C., et al., "Central Dopamingergic and 5-Hydroxytryptamingergic Effects of C3-Methylated Derivatives of 8-Hydroxyl-2-(di-n-propylamino)tetralin," *J. Med. Chem.* 1988, 31, 1130–1140.) The need for ligands with an even higher affinity and selectivity for this serotonin receptor remains. Such ligands would be useful in the imaging methods described above to monitor serotonin receptor sites.

SUMMARY OF THE INVENTION

Test results indicate that the novel compounds of Formulas I are highly selective for either the D-3 receptor or the serotonin (5-HT$_{1A}$) receptor.

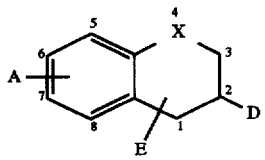

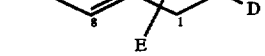

where

A is selected from the group consisting of OH and OCH$_3$ and is at the 5-, 6-, 7-, or 8-ring position;

X is selected from the group consisting of CH$_2$, O and S;

D is —N(CH$_2$CH$_2$CH$_3$)(R);

R is selected from the group consisting of H, C$_1$–C$_5$ alkyl and (CH$_2$)$_n$CH=CHR';

n is 1 or 2;

R' is selected from the group consisting of an iodine atom, a bromine atom, a methyl group and an ethyl group;

E is selected from the group consisting of H, C$_1$–C$_5$ alkyl and (CH$_2$)$_n$CH=CHR' and is at the 1- or 3-ring position;

provided that one of D and E contains the moiety (CH$_2$)$_n$CH=CHR';

or D and E may be taken together to form a ring selected from the group consisting of

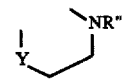

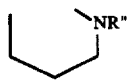

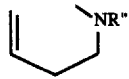

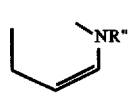

where

R" is (CH$_2$)$_n$CH=CH—R'; and

Y is selected from the group consisting of CH$_2$, O and S; and pharmaceutically acceptable salts thereof.

Tests indicate that compounds of Formula I where A is in the 7-position are highly selective for the D-3 receptor and should therefore have pharmacological activity associated with binding the D-3 receptor or, if appropriately radiolabelled, should possess utility as imaging agents for evaluation of such receptors. Tests further indicate that compounds of Formula I where A is in the 8-position are highly selective for the serotonin 5-HT$_{1A}$ receptor and should therefore have pharmacological activity associated with the binding of that receptor or, if appropriately radiolabelled, should possess utility as imaging agents for evaluation of that receptor.

This invention therefore relates to the novel compounds of Formulas I, to methods of preparing them and to methods of utilizing them as imaging agents for the evaluation of CNS D-3 or 5-HT$_{1A}$ receptors. This invention further relates to novel compounds of Formula II which are useful as intermediates for preparing radiolabelled compounds of Formula I.

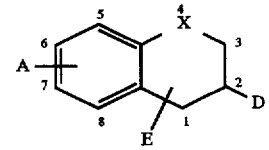

where

A and X are as defined above;

D is —N(CH$_2$CH$_2$CH$_3$)(R$_1$);

R$_1$ is selected from the group consisting of H, C$_1$–C$_5$ alkyl and (CH$_2$)$_n$CH=CHSnBu$_3$;

n is 1 or 2;

E is selected from the group consisting of H, C$_1$–C$_5$ alkyl and (CH$_2$)$_n$CH=CHSnBu$_3$ and is at the 1- or 3-ring position;

provided that one of D and E contains the moiety (CH$_2$)$_n$CH=CHSnBu$_3$;

or D and E may be taken together to form a ring selected from the group consisting of

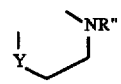

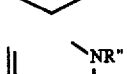

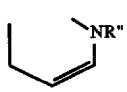

where

R" is (CH$_2$)$_n$CH=CH—SnBu$_3$; and

Y is selected from the group consisting of CH$_2$, O and S.

DETAILED DESCRIPTION OF THE INVENTION

Figure 1A:
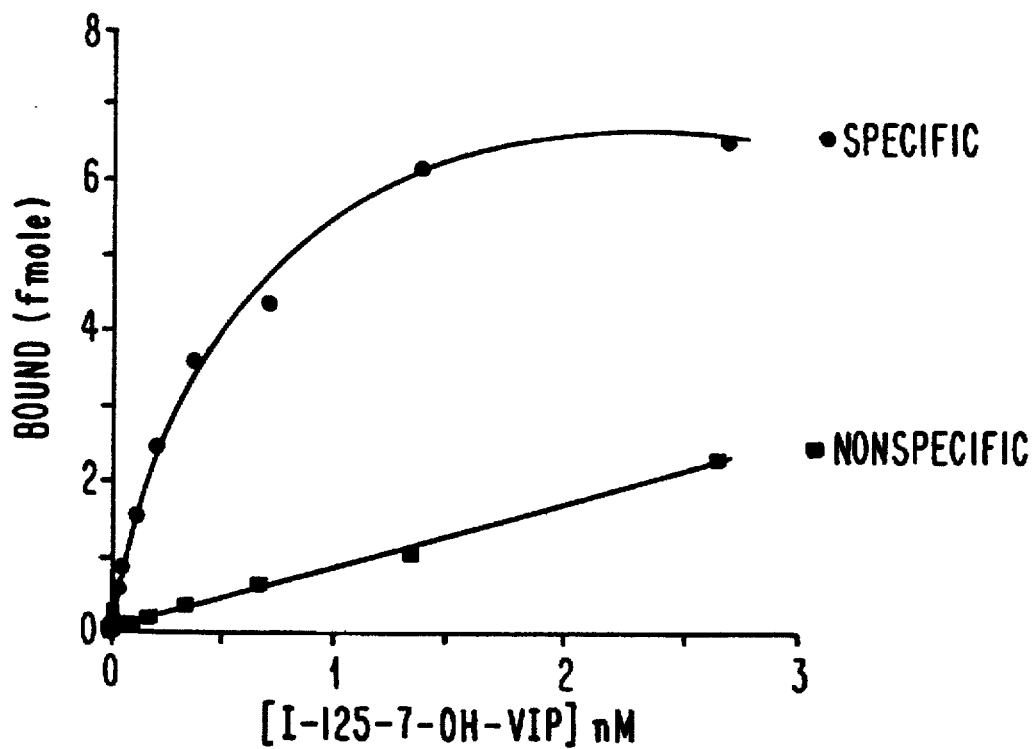
FIGS. 1A and 1B comprise saturation and scatchard plots of binding of [$^{125}$I]trans-7-OH-PIPAT in AcMNPVrD3-infected Sf9 cell membranes at 25° C. without NaCl.

Certain of the iodinated compounds of this invention may be prepared by methods analogous to that illustrated in Scheme 1 for the synthesis of trans-7-OH-PIPAT (5).

Scheme 1

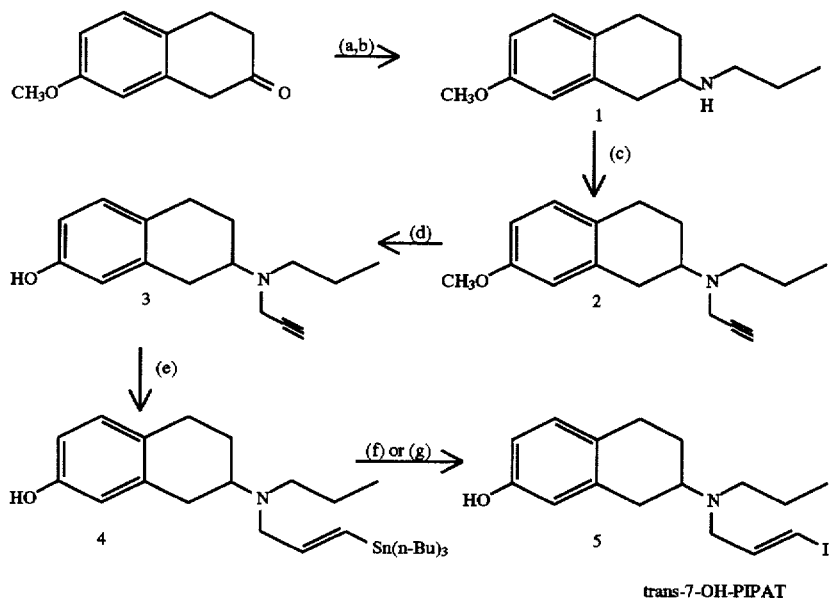

a). n-propylamine
b). PtO₂/H₂
c). propynyl chloride/K₂CO₃
d). (CH₃)₃SiI, CH₂Cl₂
e). (n-Bu)₃SnH, AIBN, toluene
f). N-Iodosuccinimide/NaI
g). H₂O₂/Na$^{125}$I Amination of 7-Methoxy-2-tetralone may be carried out with n-propylamine followed by hydrogenation in the presence of PtO₂ under hydrogen (30 psi) to give 1 in good yield (See, e.g., McDermed, J., et al., *J. Med. Chem.* 1976, 19, 547–549; McDermed, J., et al., *J. Med. Chem.* 1975, 18, 362–367.) Compound 1 is reacted with propynyl chloride to yield the desired compound 2. Deblocking of 2 with trimethylsilyliodide yields 3. When 3 is reacted with tributyltin hydride in the presence of AIBN as the catalyst, the reaction gives trans isomer 4 as its main product. The corresponding 2'-trans-iodopropenyl derivative, 5, can be prepared by reacting the trans-tributyltin derivative with sodium iodide and N-iodosuccinimide. Radioiodination with I-125 (carrier-free, Na$^{125}$I) can be carried out starting with the corresponding tributyltin derivative, 4, with hydrogen peroxide as the oxidant as reported before (Kung, M. -P., et al., *J. Nucl. Med.* 1990, 31, 648–654). The desired product, [$^{125}$I]trans-7-OH-PIPAT, may be obtained after HPLC separation.

Presented in Scheme 2 is a method of synthesis for trans-8-OH-PIPAT (8); analogous methods may be used to prepare other compounds of the invention.

Scheme 2

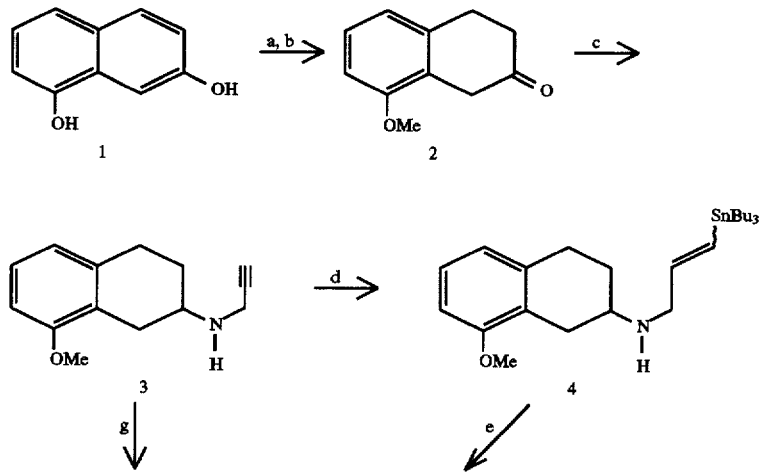

Scheme 2 (continued)

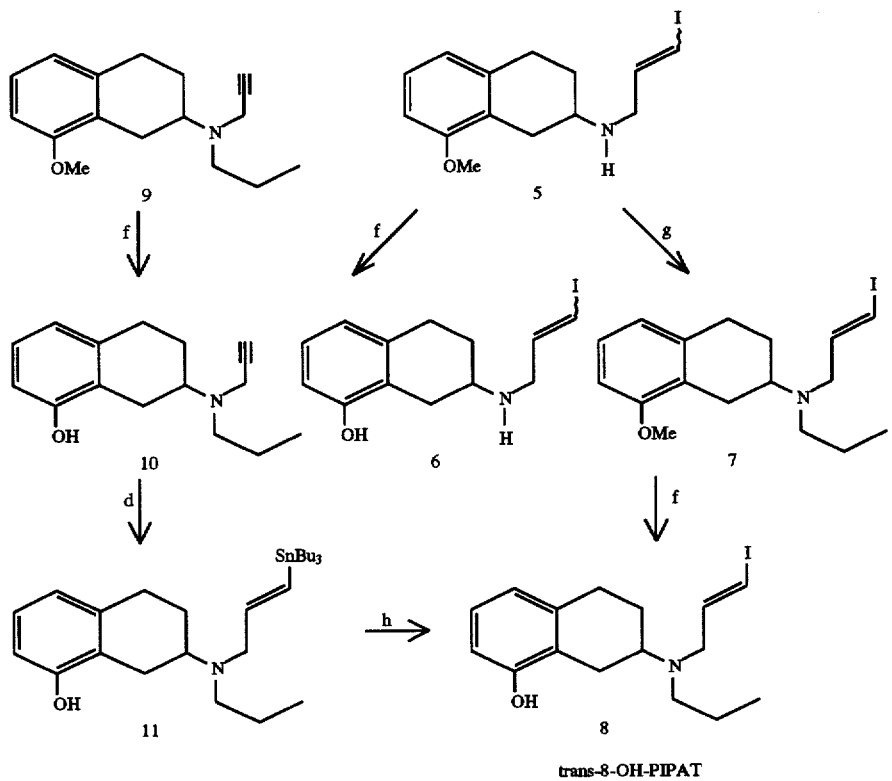

trans-8-OH-PIPAT a) Me$_2$SO$_4$, NaOH; b) Na, EtOH; HCl; c) 2-propynylamine, p-TsOH, benzene; NaCNBH$_3$, MeOH; d) HSnBu$_3$, AIBN, Toluene; e) I$_2$, CHCl$_3$; f) BBr$_3$, CH$_2$Cl$_2$; g) 1-iodopropane, K$_2$CO$_3$, EtOH; h) Na*I/H$_2$O$_2$.

As illustrated in Scheme 2, the starting mataerial, 8-methoxy-2-tetralone (2), is condensed with 2-propynylamine, followed by reduction with sodium cyanoborhydride to give 8-methoxy-2-N-propynylamnotetralin (3), in 64% yield. The acetylene derivative (3), is converted to the desired tin compound, (4)(mixture of cis and trans isomers), by reacting compound (3) with tri-n-butyltin hydride in the presence of AIBN, 2,2'-azobis(2-methylpropionitrile), as the cataylst. The corresponding iododerivative (5), a cis/trans mixture, can be obtained by reacting (4) with iodine in chloroform. Demethylating (5) by BBr$_3$ gives a mono-N-alkylated compound (6). The trans isomer of (5) can be removed and the subsequent reactions carried out. For N,N-dialkylated derivatives, trans-(5) is N-propylated first with 1-iodopropane to give (7), followed by O-demethylation of (7) using BBr$_3$ to give the desired product (8).

To produce a tri-n-butyltin derivative (11), for radioiodination, a separate reaction sequence may be used, as also illustrated in Scheme 2. Compound (3) is N-alkylated with 1-iodopropane to give the N,N-dialkylated derivative (9). Demethylation with BBr$_3$ and radical reaction with tri-n-butyltin hydride, in the presence of AIBN as the catalyst, gives the desired precursor (11) for radioiodination. Radioiodination with I-125 (no carrier added, Na$^{125}$I) can be carried out starting with the corresponding tri-n-butyltin derivative (11), with hydrogen peroxide as the oxidant.

Illustrated in Scheme 3 is a reaction for preparing compounds of the invention with a substituent in the 3-ring position. The procedure as illustrated is for 3-Me-5-OH-PIPAT, but is equally applicable to th 3-Me-6-OHm 3-Me-7-OH and 3-Me-8-OH derivatives. As a reference, see Johansson, et al., *J. Med Chem.* 30:1135 (1987).

Scheme 3

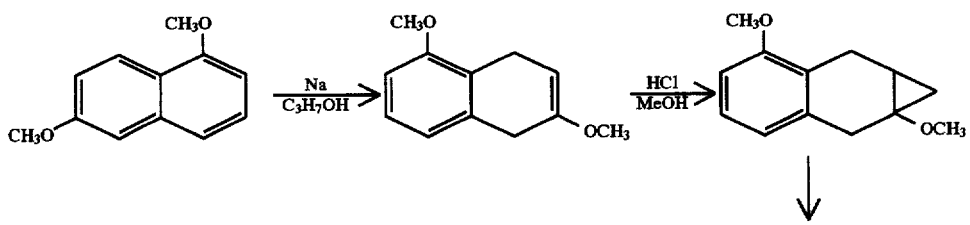

-continued
Scheme 3
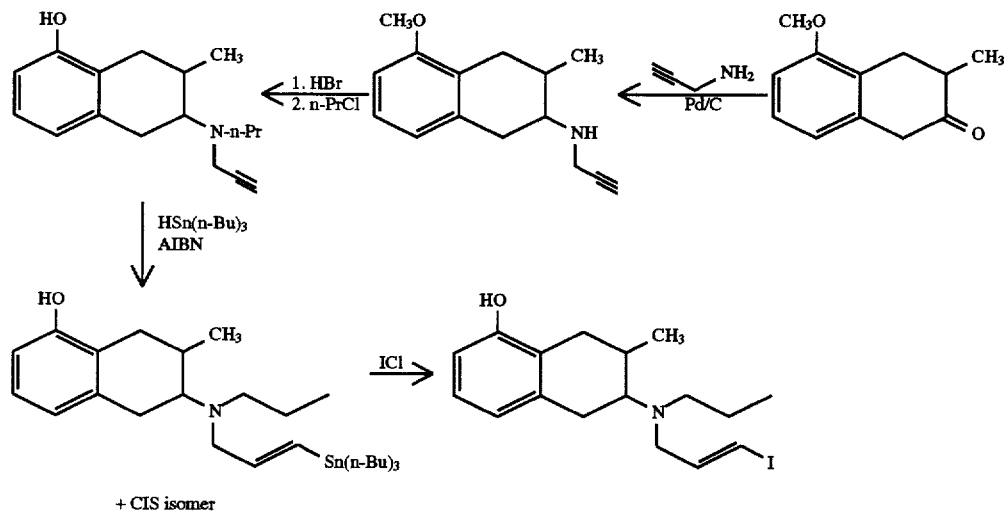
Tricyclic compounds of the invention may be made by methods analogous to that illustrated in Scheme 4:
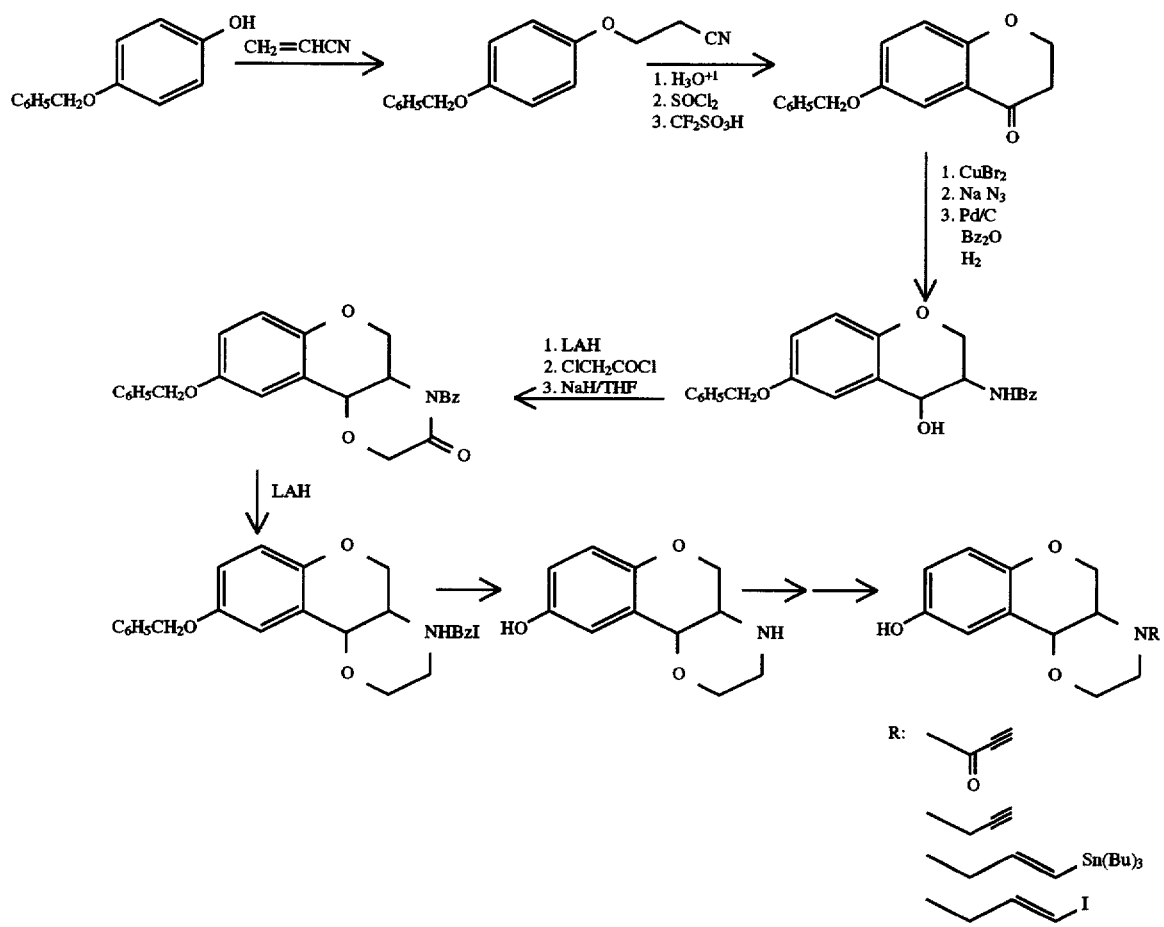

Heterocyclic compounds of the invention may be made by methods analogous to those presented above in Scheme 4 or below in Scheme 5. See, also, Wise, L. D. et al., *J. Med. Chem.* 31:688–691 (1988).
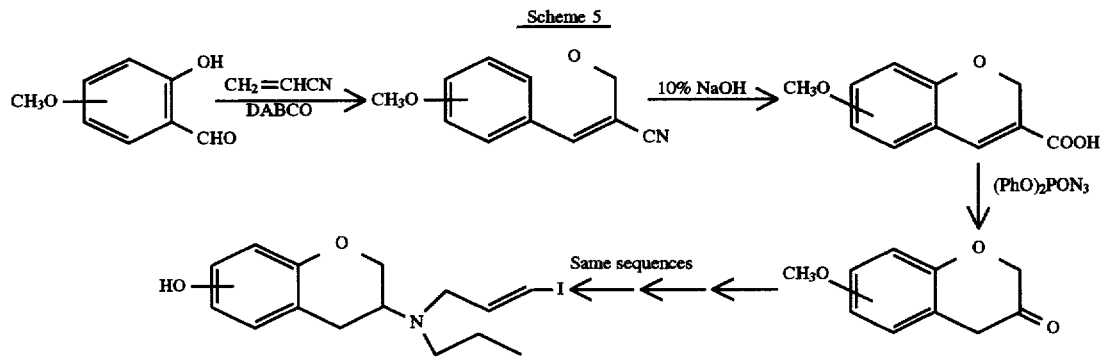
Scheme 6 illustrates the preparation of the compound 5-OH-PIPAT, and analogous methods may be used to prepare additional compounds of the invention.
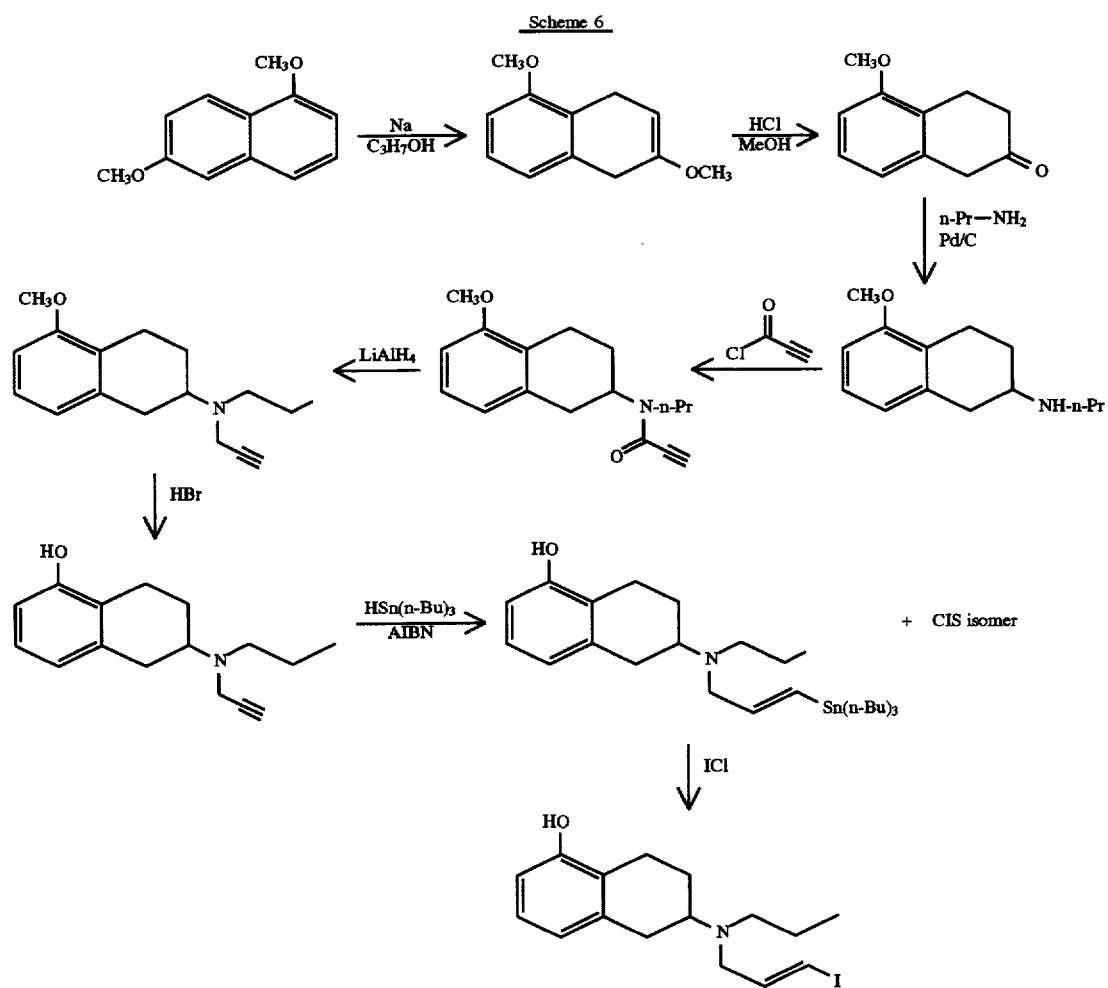

Illustrated in Scheme 7 are methods for preparing compounds of the invention in which the substituent E is other than hydrogen. Analogous methods may be used to prepare additional compounds of the invention.

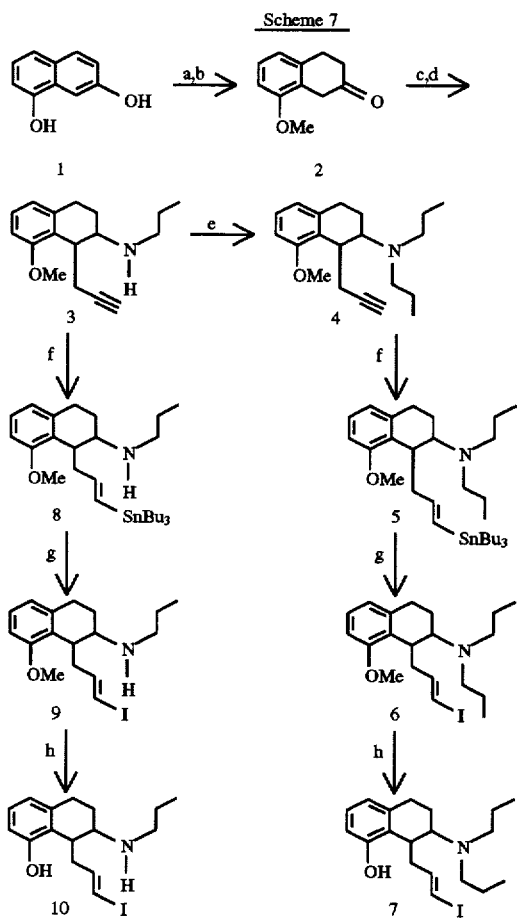

a) Me₂SO₄, NaOH; b) Na, EtOH; HCl; c) LDA, propynyl chloride, THF
d) propynylamine, p-TsOH, benzene; NaCNBH₃, MeOH;
e) 1-iodopropane, K₂CO₃, EtOH f) HSnBu₃, AIBN, Toluene;
g) I₂, CHCl₃; h) BBr₃ CH₂Cl₂

With the information provided above, one skilled in the art would be able to prepare any of the claimed compounds of this invention.

The iodinated compounds of this invention form cis and trans isomers due to the configuration of the double bond. The geometric isomers, i.e. cis vs. trans, can be readily separated by column chromatography. Tests have indicated that the cis or trans isomer is equally specific and potent.

The compounds of this invention also have a chiral center and form R- and S-isomers. These isomers can be resolved by a chiral HPLC column. Tests indicate that R-[$^{125}$I]trans-7-OH-PIPAT exhibits a two-fold increase of the binding affinity to AcMNPVrD3-infect4d Sf9 cell membranes over the unresolved racemic mixture. This invention relates to the racemic mixtures of the compounds as well as to the resolved isomers, especially the R-isomers.

When the compounds of this invention are to be used as imaging agents, they must be labelled with suitable radio-active halogen isotopes. Although $^{125}$I-isotopes are useful for laboratory testing, they will generally not be useful for actual diagnostic purposes because of the relatively long half-life (60 days) and low gamma-emission (30–65 Kev) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I (half life of 2 hours). Suitable bromine isotopes include $^{77}$Br and $^{76}$Br.

Pharmaceutically-acceptable salts of the compounds of this invention include the acid addition salts derived from non-toxic inorganic acids such as hydrochloric acid, nitric acid, phosphoric acid, sulfuric acid, hydrobromic acid, hydroiodic acid, phosphorous acid and the like. Also included are those salts derived from non-toxic organic acids such as aliphatic mono and dicarboxylic acids, phenyl-substituted alkanoic acids, hydroxy alkanoic and alkandioic acids, aromatic acids, and aliphatic and aromatic sulfonic acids.

Preferred compounds of this invention are those where, independently or in combination: (a) A is OH; (b) A is at the 7- or 8-ring position; (c) X is CH₂; (d) D is N(CH₂CH₂CH₃) ((CH₂)$_n$CH=CHR'); (e) n is 1; (f) R' is an iodine or bromine atom; (g) E is hydrogen.

Tests indicate that the binding affinity of compounds where A is OCH₃ is not as great as that of compounds where A is OH. Compounds where A is OCH₃, however, also have utility as intermediates in the production of the hydroxy compounds, as indicated in the reaction schemes presented above.

Specific examples of compounds within the scope of this invention are illustrated in Table 1.

TABLE 1

| A | X | E | D |
|---|---|---|---|
| 7-OH | CH₂ | H | N(n-Pr)(CH₂CH=CHI) |
| 7-OH | CH₂ | H | N(n-Pr)(CH₂CH₂CH=CHI) |
| 7-OH | CH₂ | H | N(n-Pr)(CH₂CH=CHCH₃) |
| 7-OH | CH₂ | H | N(n-Pr)((CH₂)₂CH=CHCH₃) |
| 7-OH | CH₂ | H | N(n-Pr)(CH₂CH=CHCH₂CH₃) |
| 7-OH | CH₂ | H | N(n-Pr)((CH₂)₂CH=CHCH₂CH₃) |
| 7-OH | O | H | N(n-Pr)(CH₂CH=CHI) |
| 7-OH | CH₂ | H | N(n-Pr)(CH₂CH₂CH=CHI) |
| 7-OH | CH₂ | H | N(n-Pr)(CH₂CH=CHCH₃) |
| 7-OH | CH₂ | H | N(n-Pr)((CH₂)₂CH=CHCH₃) |
| 7-OH | CH₂ | H | N(n-Pr)(CH₂CH=CHCH₂CH₃) |
| 7-OH | CH₂ | H | N(n-Pr)((CH₂)₂CH=CHCH₂CH₃) |
| 7-OH | S | H | N(n-Pr)(CH₂CH=CHI) |
| 7-OH | CH₂ | H | N(n-Pr)(CH₂CH₂CH=CHI) |
| 7-OH | CH₂ | H | N(n-Pr)(CH₂CH=CHCH₃) |
| 7-OH | CH₂ | H | N(n-Pr)((CH₂)₂CH=CHCH₃) |
| 7-OH | CH₂ | H | N(n-Pr)(CH₂CH=CHCH₂CH₃) |
| 7-OH | CH₂ | H | N(n-Pr)((CH₂)₂CH=CHCH₂CH₃) |
| 7-OH | CH₂ | —(CH₂)₃—(N(n-Pr)(CH₂CH=CHI))— | |
| 7-OH | CH₂ | —(CH₂)₃—(N(n-Pr)(CH₂CH=CHCH₃))— | |
| 7-OH | CH₂ | —O—(CH₂)₂—(N (n-Pr)(CH₂CH=CHI))— | |
| 7-OH | CH₂ | —CH—(CH₂)₂—(N(n-Pr)(CH₂CH=CHI))— | |
| 7-OH | CH₂ | —CH—(CH₂)₂—(N(n-Pr)(CH₂CH=CHCH₃))— | |
| 7-OH | CH₂ | —CH₂—CH=CH—(N(n-Pr)(CH₂CH=CHI))— | |
| 7-OH | CH₂ | —CH₂—CH=CH—(N(n-Pr)(CH₂CH=CHCH₃))— | |
| 7-OH | CH₂ | H | N(n-Pr)(CH₂CH=CHBr) |
| 7-OH | CH₂ | 1-CH₃ | N(n-Pr)(CH₂CH=CHI) |
| 7-OH | CH₂ | 1-CH₂CH=CHCH₃ | N(n-Pr)(CH₂CH=CHI) |
| 7-OH | CH₂ | 1-CH₂CH=CHI | N(n-Pr)(CH₂CH=CHCH₃) |
| 7-OH | CH₂ | 3-CH₃ | N(n-Pr)(CH₂CH=CHI) |
| 7-OH | CH₂ | 3-CH₂CH=CHCH₃ | N(n-Pr)(CH₂CH=CHI) |
| 7-OH | CH₂ | 3-CH₂CH=CHI | N(n-Pr)(CH₂CH=CHCH₃) |
| 7-OH₃ | CH₂ | H | N(n-Pr)(CH₂CH=CHI) |

TABLE 1-continued

| A | X | E | D |
|---|---|---|---|
| 8-OH | CH$_2$ | H | N(n-Pr)(CH$_2$CH=CHI) |
| 8-OH | CH$_2$ | H | N(n-Pr)(CH$_2$CH$_2$CH=CHI) |
| 8-OH | CH$_2$ | H | N(n-Pr)(CH$_2$CH=CHCH$_3$) |
| 8-OH | CH$_2$ | H | N(n-Pr)((CH$_2$)$_2$CH=CHCH$_3$) |
| 8-OH | CH$_2$ | H | N(n-Pr)(CH$_2$CH=CHCH$_2$CH$_3$) |
| 8-OH | CH$_2$ | H | N(n-Pr)((CH$_2$)$_2$CH=CHCH$_2$CH$_3$) |
| 8-OH | O | H | N(n-Pr)(CH$_2$CH=CHI) |
| 8-OH | CH$_2$ | H | N(n-Pr)(CH$_2$CH$_2$CH=CHI) |
| 8-OH | CH$_2$ | H | N(n-Pr)(CH$_2$CH=CHCH$_3$) |
| 8-OH | CH$_2$ | H | N(n-Pr)((CH$_2$)$_2$CH=CHCH$_3$) |
| 8-OH | CH$_2$ | H | N(n-Pr)(CH$_2$CH=CHCH$_2$CH$_3$) |
| 8-OH | CH$_2$ | H | N(n-Pr)((CH$_2$)$_2$CH=CHCH$_2$CH$_3$) |
| 8-OH | S | H | N(n-Pr)(CH$_2$CH=CHI) |
| 8-OH | CH$_2$ | H | N(n-Pr)(CH$_2$CH$_2$CH=CHI) |
| 8-OH | CH$_2$ | H | N(n-Pr)(CH$_2$CH=CHCH$_3$) |
| 8-OH | CH$_2$ | H | N(n-Pr)((CH$_2$)$_2$CH=CHCH$_3$) |
| 8-OH | CH$_2$ | H | N(n-Pr)(CH$_2$CH=CHCH$_2$CH$_3$) |
| 8-OH | CH$_2$ | H | N(n-Pr)((CH$_2$)$_2$CH=CHCH$_2$CH$_3$) |
| 8-OH | CH$_2$ | —(CH$_2$)$_3$— | (N(n-Pr)(CH$_2$CH=CHI))— |
| 8-OH | CH$_2$ | —(CH$_2$)$_3$(N(n-Pr)(CH$_2$CH=CHCH$_3$))— | |
| 8-OH | CH$_2$ | —O—(CH$_2$)$_2$— | (N(n-Pr)(CH$_2$CH=CHI))— |
| 8-OH | CH$_2$ | —CH—(CH$_2$)$_2$— | (N(n-Pr)(CH$_2$CH=CHI))— |
| 8-OH | CH$_2$ | —CH—(CH$_2$)$_2$— | (N(n-Pr)(CH$_2$CH=CHCH$_3$))— |
| 8-OH | CH$_2$ | —CH$_2$—CH=CH— | (N(n-Pr)(CH$_2$CH=CHI))— |
| 8-OH | CH$_2$ | —CH$_2$—CH=CH— | (N(n-Pr)(CH$_2$CH=CHCH$_3$))— |
| 8-OH | CH$_2$ | H | N(n-Pr)(CH$_2$CH=CHBr) |
| 8-OH | CH$_2$ | 1-CH$_3$ | N(n-Pr)(CH$_2$CH=CHI) |
| 8-OH | CH$_2$ | 1-CH$_2$CH=CHCH$_3$ | N(n-Pr)(CH$_2$CH=CHI) |
| 8-OH | CH$_2$ | 1-CH$_2$CH=CHI | N(n-Pr)(CH$_2$CH=CHCH$_3$) |
| 8-OH | CH$_2$ | 3-CH$_3$ | N(n-Pr)(CH$_2$CH=CHI) |
| 8-OH | CH$_2$ | 3-CH$_2$CH=CHCH$_3$ | N(n-Pr)(CH$_2$CH=CHI) |
| 8-OH | CH$_2$ | 3-CH$_2$CH=CHI | N(n-Pr)(CH$_2$CH=CHCH$_3$) |
| 8-OH$_3$ | CH$_2$ | H | N(n-Pr)(CH$_2$CH=CHI) |

Tests indicate that the 7-OH tetralin derivatives of this invention, especially 7-hydroxy-2-[N-3'-(1-iodo-1'E-propenyl)-N-n-propyl]-aminotetralin (7-OH-PIPAT) demonstrate unique high affinity and selectivity toward the D3 receptor. These compounds should be useful for studying the D3 dopamine receptor in in vivo and in vitro systems. The information generated will be very important for understanding the pharmacology as well as the relevance of D3 dopamine receptors on the mechanism of action of neuroleptics for treatment and management of patients with mental illness. These tetralin derivatives may also have direct pharmacological activity and be useful for treatment of central nervous system disorders.

Tests also indicate that the 8-OH tetralin derivatives of this invention, especially 8-hydroxy-2-(N-n-propyl-N-3'-iodo-2'-propenyl)amino-tetralin (8-OH-PIPAT), demonstrate unique high affinity and selectivity toward serotonin 5-HT$_{1A}$ sites. When the compounds are labelled with a radioactive ion, such as $^{123}$I, the serotonin reuptake sites may be imaged by means such as PET and SPECT. Such imaging of the human brain may provide or suggest direct information on the location and quantitation of the 5-HT$_{1A}$. Direct assessment on the status of serotonin 5-HT$_{1A}$ receptor may provide evidence of how the selective 5-HT$_{1A}$ agonists regulate the receptor sites and may also be a diagnostic tool for individualizing the dosage for this class of antianxielytic agents. The 8-OH compounds which are not radiolabelled will also bind to 5-HT$_{1A}$ sites, suggesting therapeutic utility or use in in vitro binding studies.

The radiolabelled compounds of this invention lend themselves easily to formation from materials which could be provided to users in kits. Kits for forming the imaging agents can contain, for example, a vial containing a physiologically suitable solution of an intermediate of Formula II in a concentration and at a pH suitable for optimal complexing conditions. The user would add to the vial an appropriate quantity of the radioisotope, e.g., Na$^{123}$I, an oxidant, such as hydrogen peroxide. The resulting labelled ligand may then be administered intravenously to a patient, and receptors in the brain imaged by means of measuring the gamma ray or photo emissions therefrom.

The following examples are provided to further illustrate this invention and are not intended to limit its scope. In these examples, $^1$H-NMR were recorded on a Bruker AM-300 (300 MHz) or a Bruker AM-500 (500 MHz) spectrometer. The chemical shifts were reported in ppm downfield from an internal tetramethylsilane standard. Infrared spectra were obtained with a Mattson Polaris FT-IR spectrophotometer. HPLC was performed on a model Rabbit HP of Rainin Instrument Co. Inc. (Emeryville, Calif.) using a reverse phase column: PRP-1 of Hamilton Inc. (Reno, Nev.). Mass spectra were performed on a mass-spectrometer VG 70-70 HS with chemical ionization (CI), using methane or ammonia gas. Elemental analysis was performed by Atlantic Microlabs Inc. (Norcross, Ga.). 7-methoxy-2-tetralone, 1-iodo-propane, propynyl chloride, benzyl-amine, n-propylamine, tributyltin hydride, a,a'-azoisobutironitrile (AIBN), HBr 48%, trimethylsilyliodide were purchased from Aldrich (Milwaukee, Wis.),$_n$N-Iodosuccinimide was purchased from Sigma (Saint-Louis, Mo.). [125I]-NaI was provided by DuPont (Boston, Mass.).

EXAMPLE 1

Preparation of 2'-trans-7-Hydroxy-2-[N]3'-(1-iodo-2E-propenyl)-N-n-propyl]amino]tetralin (trans-7-OH-PIPAT, 5)

a. 7-Methoxy-2-(N-n-propylamino)-tetralin (1):

A solution of 7-methoxy-2-tetralone (32 mmol, 5 g), n-propylamine (60 mmol, 5 mL), acetic acid (60 mmol, 4 mL), molecular sieves 3A (5 g) in ethanol (25 mL) was stirred at room temperature for 2.5 hrs. The solution was filtered on paper in a Paar bottle and the reduction was carried out with PtO$_2$ (100 mg) as the catalyst, under 30 PSI of hydrogen. When the pressure dropped to 6 PSI (30 min.), the catalyst was removed by elution onto a column (celite 545) with chloroform. The eluent was concentrated under vacuum. The residue, a brown oil, was converted to solid by formation of hydrogen chloride salt in ether/HCl. Several recrystallizations in ether/methanol (60/40) afforded the final product (1) as white crystals (4.28 g, 61% yield).

FT-IR (neat) n (cm$^{-1}$): 3350 (m, 1; NH), 3030 (m, f; arom.), 2950 (s, f; aliph.), 1600, 1520, 1250; $^1$H-NMR (CDCl$_3$) d (ppm): 6.99 (d, 1H, arom. J=8.4), 6.70–6.67 (dd, 1H, arom. J=8.4, 2.7), 6.62 (d, 1H, arom. J=2.7), 3.76 (s, 3H, O—CH$_3$), 3.04–2.52 (m, 9H, CH—N, N—CH$_2$, 2 Ar—CH$_2$), 1.55 (m, 4H, CH$_2$—CH$_3$, Ar—CH$_2$—CH$_2$), 1.22 (s, 1H, NH), 0.95 (t, 3H, CH$_3$); C, H, N analysis: C$_{14}$H$_{22}$NO, HCl.

Elemental analysis data:

| Compound | Element | Calculated | Found |
|---|---|---|---|
| 1 | C | 65.74 | 65.77 |
|   | H | 8.67  | 8.69  |
|   | N | 5.48  | 5.51  | b. 7-Methoxy-2-(N-propynyl -N-n-propylamino)-tetralin (2):

Compound 1. HCl was dissolved in dichloromethane (200 mL) and NaOH 1N was added until the acidity of the aqueous layer reached pH 9. The organic layer was washed with brine (50 mL), dried ($Na_2SO_4$) and concentrated under vacuum to give the neutral amine 1, which was used for the following alkylation reaction. Propynyl chloride (3 mmol, 1.5 mL) was added dropwise to a solution containing the neutral amine 1 (2.48 mmol, 546 mg) and $K_2CO_3$ (3 mmol, 400 mg) in ethanol (4 mL), while temperature of the reaction mixture was maintained at 0° C. The mixture was refluxed overnight (18 hr). The salts were filtered off and the liquid phase was neutralized with $NaHCO_3$ (5%). The product was extracted by dichloromethane (3×20 mL). The organic layers were pooled, washed with brine (20 mL) and dried over anhydrous $Na_2SO_4$. The desired compound, 2, was purified by column chromatography (silica gel, ethyl acetate) and appeared as a yellow oil (557 mg, 87% yield).

FT-IR (neat) n ($cm^{-1}$): 3300 (m, f; acetylene), 3020 (m, f; arom.), 2950–2800 (s, f; aliph.), 2100 (w, f; acetylen.), 1620, 1500, 1230; $^1$H-NMR ($CDCl_3$) d (ppm): 7.01 (d, 1H, arom. J=8.1), 6.72–6.69 (dd, 1H, arom. J=8.1, 2.5), 6.65 (d, 1H, arom. J=2.7), 3.79 (s, 3H, O—$CH_3$), 3.55 (d, 2H, $CH_2$-propynyl, J=2.4), 3.04–2.62 (m, 5H, CH—N, 2 Ar—C$\underline{H}_2$), 2.19 (t, 1H, acetylen., J=2.4), 1.71–1.50 (m, 4H, C$\underline{H}_2$—$CH_3$, Ar—$CH_2$—$C\underline{H}_2$), 0.94 (t, 3H, $CH_3$, J=7.4); MS: (CI, high resolution) M+H: Calc: 258.1858, Found: 258.1833.

c. 7-Hydroxy-2-(N-propynyl -N-n-propylamino)-tetralin (3):

Demethylation of 2 was achieved by adding trimethylsilyl iodide (3 mL) to a solution of 2 (903 mg, 3.5 mmol) in anhydrous chloroform (2 mL). The mixture was stirred at room temperature under nitrogen for 52 hrs. The reaction was quenched with methanol (15 mL) and the solution was condensed under vacuum. The dark residue was dissolved in 20 mL of $NaHSO_3$ solution (5%), the pH was adjusted to 7 ($NaHCO_3$) and the crude product was extracted by dichloromethane (3×15 mL). The organic layers were pooled, washed with brine (20 mL) and dried over anhydrous $Na_2SO_4$. The solvent was removed under reduced pressure and the product was purified by column chromatography (silica gel, hexanes/ethyl acetate: 75/25). A yellow oil was obtained (291 mg, 40% yield).

FT-IR (neat) n ($cm^{-1}$): 3400 (s, f; OH), 3300 (s, f; acetylene), 3030 (m, f; arom.), 2970–2700 (s, f; aliph.), 2050 (w, f; acetylene), 1750, 1600, 1500; $^1$H-NMR ($CDCl_3$) d (ppm): 6.91 (d, 1H, arom. J=8.1), 6.59–6.56 (dd, 1H, arom. J=8.1, 2.7), 6.53 (d, 1H, arom. J=2.4), 3.52 (d, 2H, $CH_2$-propynyl, J=2.4), 2.96–2.52 (m, 7H, 2 Ar—$CH_2$, CH—N, N—$CH_2$), 2.17 (t, 1H, acetylene, J=2.4), 1.55–1.47 (m, 4H, C$\underline{H}_2$—$CH_3$, Ar—$CH_2$—$C\underline{H}_2$), 0.90 (t, 3H, $CH_3$); MS: (CI, high resolution) M+H: Calc: 244.1701, Found: 244.1716.

d. 2'-trans-7-Hydroxy-2-[N-n-propylamino-N-(3'-tributylbutyltin-2'-propenyl)]-tetralin (4):

A flask purged under nitrogen, containing the alkynyl derivative, 3, (283 mg, 1.38 mmol), AIBN (5 mg), tributyltin hydride (300 uL) and anhydrous toluene (4 mL) was refluxed for 4 hrs. When the mixture was cooled, broken ice (10 g) and $NH_4Cl$ 10% (20 mL) were added. The crude product was extracted in ether (3×20 mL). The organic layers were pooled, washed with brine (15 mL), dried over anhydrous $Na_2SO_4$ and the solvent was removed under reduced pressure. After purification by column chromatography (silica gel, hexanes/Ethyl acetate: 75/25) 4, (66 mg) was obtained as a yellow oil. The coupling constant of the CH=C$\underline{H}$ was 14.2 Hz, suggesting that the trans isomer was obtained.

FT-IR (neat) n ($cm^{-1}$): 3500–3300 (m, 1;OH), 3030 (m, f; arom.), 2950–2900 (s, f; aliph.), 1620, 1500, 1270; $^1$H-NMR ($CDCl_3$) d (ppm): 6.91 (d, 1H, arom. J=8.2), 6.59–6.55 (m, 2H, arom., $CH_2$—C$\underline{H}$=C), 6.53 (d, 1H, arom. J=2.6), 6.23–6.20 (d, 1H, CH=C$\underline{H}$-I, J=14.2), 3.17 (d, 2H C$\underline{H}_2$—CH=C, J=5.2), 2.94 (s, 1H, OH), 2.82–2.46 (m, 7H, CH—N, N—$CH_2$, 2 Ar—$CH_2$), 1.57–1.42 (m, 4H, C$\underline{H}$—$CH_2$, Ar—$CH_2$—$C\underline{H}_2$), 0.85 (m, 3H, $CH_3$); MS: (CI, high resolution) M+H: Calc: 372.0824, Found: 372.0802

The corresponding cis isomer was also isolated by the same column chromatography procedure (9 mg). Overall yield was 20% and cis/trans ratio was 0.88. The cis isomer was not fully characterized due to insufficient quantity of this compound. Additional work in this area is being carried out and a full paper describing the preparation and characterization of this series of compounds will be forthcoming.

e. 2'-trans-7-Hydroxy-2-[N-3'-(1-iodo-2E-propenyl)-N-n-propyl]amino]tetralin (trans-7-OH-PIPAT, 5):

A solution of tributyltin precursor, 4, (60 mg, 0.11 mmol) N-iodo-succinimide (0.11 mmole) and sodium iodide (0.22 mmoles) in 1.5 mL of methanol/acetic acid (90/10), was stirred at room temperature under nitrogen for 3 hrs. The reaction was terminated by introducing water (2 mL) and $NaHSO_3$ 5% (5 mL). After evaporation of the volatiles under reduced pressure, the pH was adjusted to 7 with NaOH (1N). The crude product was extracted into ether (2×10 mL). The organic layers were pooled, washed with brine (5 mL), dried over anhydrous $Na_2SO_4$ and the solvent was removed under reduced pressure. After purification by column chromatography (silica gel, hexanes/ethyl acetate/$NH_4OH$: 60/40/0.5) afforded 5 as a yellow oil (12 mg, 29% yield).

FT-IR (neat) n ($cm^{-1}$): 3500–3300 (m, 1; OH), 3030 (m, f; arom.), 2950–2900 (s, f; aliph.), 1620, 1500, 1270; $^1$H-NMR ($CDCl_3$) d (ppm): 6.91 (d, 1H, arom. J=8.2), 6.59–6.55 (m, 2H, arom., $CH_2$—C$\underline{H}$=C) , 6.53 (d, 1H, arom. J=2.6), 6.23–6.20 (d, 1H, CH=C$\underline{H}$—I, J=14.2) , 3.17 (d, 2H C$\underline{H}_2$—CH=C, J=5.2) , 2.94 (s, 1H, OH), 2.82–2.46 (m, 7H, CH—N, N—$CH_2$, 2 Ar—$CH_2$), 1.57–1.42 (m, 4H, C$\underline{H}$—$CH_2$, Ar—$CH_2$—$C\underline{H}_2$), 0.85 (m, 3H, $CH_3$); MS: (CI, high resolution) M+H: Calc: 372.0824, Found: 372.0802

EXAMPLE 2

Preparation of [$^{125}$I]trans-7-OH-PIPAT($^{125}$I]5)

No-carrier-added [$^{125}$I]trans-7-OH-PIPAT($^{125}$I]5) was prepared by an iododestannylation reaction similar to the procedure reported previously (8). Hydrogen peroxide (50 ml, 3% w/v) was added to a mixture of 50 ml of tributyltin precursor (1mg/ml EtOH), 50 ml of 1N HCl and I-125 (2–3 mCi) in a sealed vial. The reaction was allowed to proceed for 20 min at room temperature, and was then terminated by addition of 0.1 ml of sodium bisulfite (300 mg/ml). The reaction mixture was extracted with ethyl acetate (3×1 ml) after neutralization with saturated $NaHCO_3$ solution. The extracted ethyl acetate layers were evaporated to dryness, and the remaining residue was dissolved in EtOH and purified by HPLC using a reverse phase column (PRP-1 column, Hamilton Co., Reno, Nev.) eluted with an isocratic solvent of 80% acetonitrile-20% pH 7.0 buffer (5 mM 3,3'-dimethylglutaric acid). The fractions containing the desired product were collected, condensed and re-extracted with ethyl acetate (3×1 ml). The no-carrier-added final product (purity >98%) was evaporated to dryness and redissolved in 100 ml of 50% EtOH with 100 mg ascorbic acid added as an anti-oxidant. The final product [$^{125}$I]trans-7-OH-PIPAT([$^{125}$I]5) was stored at −20° C. The stability of the product was evaluated from three preparations and was found to be stable for at least four weeks (>95% pure, analyzed by HPLC).

EXAMPLE 3

Binding Affinity of trans-7-OH-PIPAT in Comparison to Other Ligands a. Preparation of membranes of AcMNPVrD2 and AcMNPVrD3 infected Sf9 cells The Sf9 cells were routinely grown at 27° C. in TNM-FH medium supplemented with 10% heat-inactivated fetal bovine serum (FBS, HyClone, Logan, Utah) and penicillin/streptomycin. TNM-FH medium consists of Grace's Anatherea insect medium (GIBCO, Gaithersburg, Md.) supplemented with 3.3 g/l TC yeastolate (Difco, Detroit, Mich.) and 3.3 g/l lactalbumin hydrolysate (Difco). Cells were maintained either as monolayers in Falcon T75 flasks (Becton-Dickinson, Oxnard, Calif.) or in suspension in spinner flasks (Bellco, Vineland, N.J.) according to the procedures of Summers and Smith.

Full-length D2 dopamine receptor cDNAs amplified from a rat striatal library were subcloned into the Pst site of the baculovirus transfer vector pVL1393. Restriction digestion confirmed the ligation and demonstrated the proper orientation of the insert. The fidelity of pVL1393-rD2$_L$ and pVL1393-rD2$_S$ was confirmed by dideoxy double-stranded DNA sequencing. The construction of pVL1393-rD3 was previously described. Plasmid DNA was isolated by alkaline dialysis and purified by CsCl density gradient centrifugation and overnight dialysis for transfection of Sf9 cells. Transfer of D3 or D2 dopamine receptor cDNA into the wild-type *Autographa californica* multiple nuclear polyhedrosis virus (AcMNPV) genome was accomplished by in vivo homologous recombination. A monolayer of Sf9 cells (approximately 2×10$^6$ cells/T25 plate) was cotransfected by calcium phosphate precipitation, with 1 mg of AcMNPV DNA (provided by Dr. Max Summers, Texas A&M University, College Station, Tex.) and 2 mg of recombinant transfer vector DNA. Five days after cotransfection, the supernatant from the transfection culture was serially diluted and used to infect fresh monolayers of Sf9 cells that were subsequently overlaid with 1.5% SeaPlaque agarose (FMC Bioproducts, Rockland, Md.) for plaque purification. Putative recombinant viral plaques were chosen by visual screening for occlusion-negative plaques and used to infect 1×10$^6$ Sf9 cells in a 6-well plate (CoStar, Cambridge, Mass.). Four days after infection, cells were harvested and membranes were prepared. An aliquot of membranes was used for radioligand binding. Positive recombinant virus particles, collected from cells that demonstrated specific binding for [$^{125}$I]NCQ298, were subjected to an additional plaque purification assay. Expression of D2 receptors in the membrane homeogenates of AcMNPVrD2L (or AcMNPVrD2S) infected Sf9 cells were evaluated by binding experiments using [$^{125}$I]NCQ298. The pharmacological specificity established by the competition experiments, indicated that a profile characteristic of D2 receptors was observed. The membrane homogenates of AcMNPVrD3 infected Sf9 cells were prepared as described. Briefly, the harvested cells were centrifuged, resuspended and homogenized in buffer containing 50 mM Tris, pH7.4, 150mM NaCl, 10 mM EDTA and a mixture of protease inhibitors (1 mg/ml aprotinin, 1 mg/ml leupeptin, 1 mg/ml soybean trypsin inhibitor, 10 mg/ml PMSF). The final pellets obtained were resuspended in the same buffer and kept at −20° C. for radioligand binding assays.

b. Binding of [$^{125}$I] trans-7-OH-PIPAT (5)

Binding assays were performed in glass tubes (12×75 mm) in a final volume of 0.2 ml. The buffer used for the dilution contained 50 mM Tris, pH 7.4, and the protease inhibitors mixture. In saturation experiments, increasing concentrations of [$^{125}$I]trans-7-OH-PIPAT ([$^{125}$I]5)(0.01–2 nM) in 100 µl buffer were incubated with 50 µl of AcMNPVrD3 (or AcMNPVrD2) infected Sf9 cell homogenates (200 times dilution with above buffer containing 0.2% BSA). The competition experiments were performed in the presence of 120 mM NaCl. Each drug, at concentrations up to 10$^{-5}$ M, was examined for its ability to displace [$^{125}$I] trans-7-OH-PIPAT binding at a ligand concentration of 0.1 nM. After incubation for 30 min at 37° C. or 90 min at 25° C., the bound ligand was separated from the free ligand by filtration through glass fiber filters No. 25 (Schleicher & Schuell, Keene, N.H.) soaked with 0.2% protamine free base. The filters were then washed twice with 4 ml of ice-cold buffer (containing 50 mM Tris-HCl, pH 7.4) and the radioactivity on the filters was counted in a gamma counter (Packard 5000) with 70% efficiency. The nonspecific binding was defined with either 10 µM (+)butaclamol or 1 µM 7-OH-DPAT. Both Scatchard and competition experiments were analyzed using the iterative nonlinear least-square curve-fitting program LIGAND. Results are presented in Tables 2 and 3 and in FIG. 1.

TABLE 2

Inhibition Constants for the Binding of [$^{125}$I]NCQ298 Toward D2 and D3 Dopamine Receptors Expressed in Sf9 Cells

|  | D2 | D3 | Ratio |
| --- | --- | --- | --- |
|  | Ki (nM ± SE) | Ki (nM ± SE) | D2/D3 |
| Ligand* (7-OH-DPAT) | 142 ± 14.2 | 2.90 ± 0.50 | 48.9 |
| trans-7-OH-PIPAT | 265 ± 36 | 1.85 ± 0.37 | 143 |

TABLE 3

Potencies of various compounds to displace [$^{125}$I]trans-7-OH-PIPAT from D3 receptors (expressed in Sf9 cells)

| Compound | Receptor type | Ki (nM ± SE) | Hill Co. |
| --- | --- | --- | --- |
| trans-7-OH-PIPAT,5 | D3 | 0.99 ± 0.08 | 1.02 |
| 7-OH-DPAT | D3 | 1.81 ± 0.43 | 0.87 |
| Raclopride | D2/D3 | 9.25 ± 2.3 | 0.78 |
| Haloperidol | D2/D3 | 14.3 ± 3.1 | 0.68 |
| (+)Butaclamol | D1/D2/D3 | 3.91 ± 0.86 | 0.76 |
| Dopamine | DA | 49.3 ± 5.4 | 0.85 |
| Quinpirole | D3 | 5.65 ± 0.62 | 0.86 |
| SCH23390 | D1 | 768 ± 150 | 0.80 |
| WB4101 | a1 | 107 ± 13 | 0.96 |
| 8-OH-DPAT | 5-HT$_{1A}$ | 248 ± 29 | 0.78 |
| Mianserin | 5-HT$_2$/HT$_{1c}$ | 1524 ± 228 | 1.03 |
| Yohimbine | a2 | 2430 ± 146 | 0.97 |
| 5-HT | 5-HT | 2338 ± 420 | 0.90 |
| (±)Propranolol | b | >5000 |  |
| Naloxone | opiate | >20000 |  |

[$^{125}$I]trans-7-OH-PIPAT,[$^{125}$I]5, (0.1–0.2 nM) was incubated at 37° C. with 120 mM NaCl in the presence of the indicated compounds at 9–11 concentrations, in membrane preparations of AcMNPVrD3-infected Sf9 cells. Values are from 2–3 independent determinations in duplicate.

c. Results

Figure 1B:
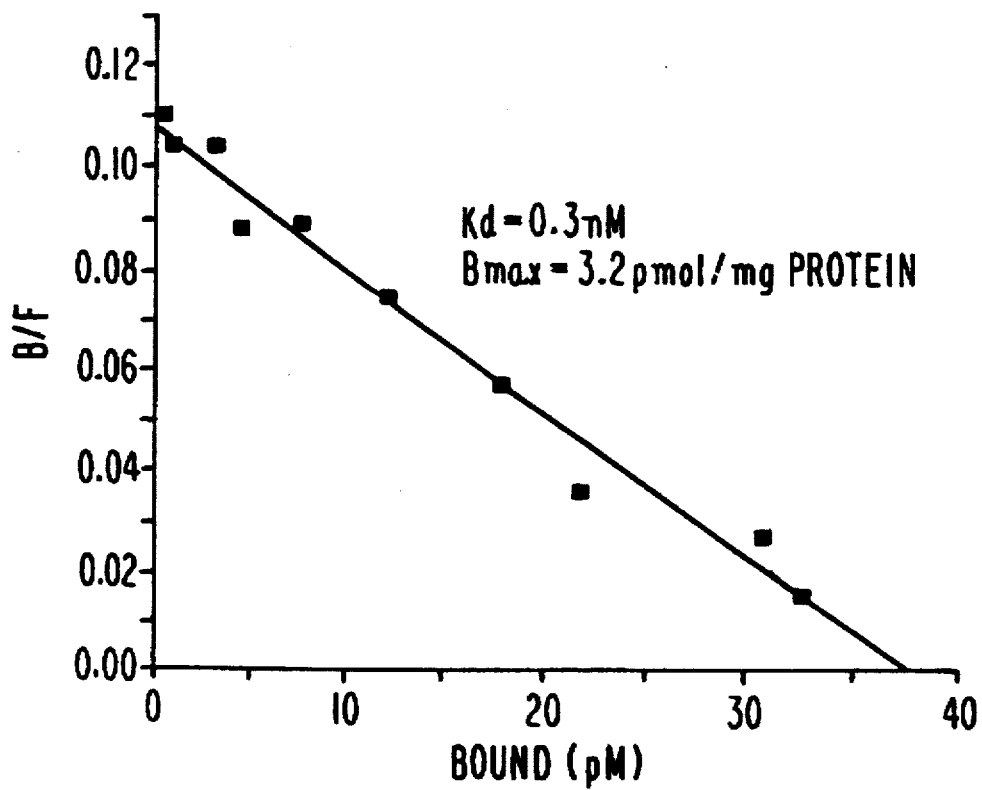

Both trans-7-OH-PIPAT and 7-OH-DPAT were found to be selective with excellent affinity for the D3 receptor (Table 2). The radioactive labeled compound, [$^{125}$I]trans7-OH-PIPAT displayed saturable and high specific binding to the membranes. Nonspecific binding accounted for a small fraction of the total binding (approximately 10% at $K_d$). In addition, [$^{125}$I]trans7-OH-PIPAT revealed one site binding (Hill coefficient approx. 1) with a $K_d$ value of 0.13 nM (FIG. 1). The $B_{max}$ obtained for this iodinated ligand was 3–4 pmol/mg protein, comparable to that measured with [$^{125}$I]NCQ298 in the same system. In contrast to [$^{125}$I]NCQ298, [$^{125}$I]trans-7-OH-PIPAT showed no specific binding toward dopamine $D_{2L}$ and $D_{2S}$ receptors expressed in Sf9 cells (data not shown).

Competition experiments performed with [$^{125}$I]trans-7-OH-PIPAT in AcMNPVrD3 infected Sf9 cell membranes revealed that several known D2 and D3 ligands, including 7-OH-DPAT, (+) butaclamol and haloperidol have high affinity for the D3 receptor. In contrast, the D1 selective agonist, SCH23390, and ligands for other receptors such as WB4101, mianserin, yohimbine and naloxone, displayed moderate to low affinity (Table 3). The high affinity observed for the dopamine agonists, quinpirole ($K_i$=5.6 nM) and dopamine ($K_i$=49.3 nM), is consistent with a similar study using D3 receptors expressed in CHO cells (Levesque, D., et al, *Proc. Natl. Acad. Sci.* 1992, 89, 8155–8159), suggesting the same binding characteristics for D3 receptors with these two ligands.

EXAMPLE 4

Additional In Vitro Binding Studies

The in vitro binding of [$^{125}$I]trans-7-OH-PIPAT was compared to that of structurally related compounds. The results are presented in Table 4.

a. D2/Sf9 Cell Membrane Homogenate Preparation

The binding assays were performed by incubating 50 ml of tissue preparation containing 10–15 mg of proteins with 0.05 nM [$^{125}$I]-NCQ298 and various concentrations of competitors in a total volume of 0.2 ml assay buffer (50 mM Tris-HCl, 120 mM NaCl, 5 mM KCl, 2 mM CaCl$_2$ and 1 mM MgCl$_2$). Incubation was performed for 20 min. at 37° C. and the samples were rapidly filtered and washed with cold assay buffer. The filters containing the bound radioactivity were then counted in a gamma counter with 70% efficiency. The non-specific binding was obtained in the presence of 10 mM (+)butaclamol.

b. D3/Sf9 cell membrane homogenate preparation:

Membranes from AcMNPV-rD3 infected Sf9 cells were prepared. Membrane binding assay using [$^{125}$I]-NCQ298 was initiated by the addition of 50 ml of tissue to 150 ml of solution containing 50 mM Tris-HCl, pH 7.4, 120 mM NaCl, 10 mM EDTA, 0.1% BSA, 0.1 nM [$^{125}$I]-NCQ298 and various concentrations of competitors. Assays were incubated at 37° C. for 20 min. then filtered and washed as described above.

TABLE 4

Inhibition Constants for the Binding of [$^{125}$I]NCQ298 Toward D2 and D3 Dopamine Receptors Expressed in Sf9 Cells

| Ligand* | D2 Ki (nM) | HC | D3 Ki (nM) | HC | Ratio D2/D3 |
|---|---|---|---|---|---|
| (7-MeO-MPAT) | 5176 ± 0.96 | 0.96 | 1310 ± 249 | 0.97 | 4.0 |
| (7-OH-MPAT) | 620 ± 124 | 0.80 | 3.25 ± 0.45 | 0.80 | 191 |
| (7-MeO-DPAT) | 2167 ± 216 | 0.95 | 280 ± 36 | 0.98 | 7.7 |
| (7-OH-DPAT) | 142 ± 14.2 | 1.02 | 2.90 ± 0.5 | 0.85 | 48.9 |
| (8-I-7-OH-DPAT) | 353 ± 31 | 0.92 | 21.3 ± 2.9 | 0.85 | 16.6 |
| (7-MeO-BAT) | 5884 ± 471 | 0.78 | 1873 ± 224 | 0.80 | 3.1 |
| (7-OH-BAT) | 1864 ± 261 | 0.80 | 391 ± 47 | 1.00 | 4.8 |
| (7-OH-PPAT) | 378 ± 45 | 0.99 | 9.2 ± 0.6 | 0.80 | 41.1 |
| (7-MeO-PIPAT) | 1383 ± 193 | 1.22 | 257 ± 31 | 0.93 | 5.4 |
| (7-OH-PIPAT) | 265 ± 48 | 0.96 | 1.85 ± 37 | 0.93 | 143 |

*7-MeO-MPAT = 7-Methoxy-2-N-n-Propylaminotetralin
7-OH-MPAT = 7-Hydroxy-2-N-n-Propylaminotetralin
7-MeO-DPAT = 7-Methoxy-2-N,N-n-Dipropylaminotetralin
7-OH-DPAT = 7-Hydroxy-2-N,N-n-Dipropylaminotetralin
8-I-7-OH-DPAT = 7-Hydroxy-8-Iodo-2-N,N-n-Dipropylaminotetralin
7-MeO-BAT = 7-Methoxy-2-N-Benzylaminotetralin
7-OH-BAT = 7-Hydroxy-2-N-n-Benzylaminotetralin
7-OH-PPAT = 7-Hydroxy-2-(-Propargyl-N-n-Propyl)-Aminotetralin
7-MeO-PIPAT = 7-Methoxy-2-[N-3'-(1'-Iodo-1'E-Propenyl)-N-n-Propylamino]tetralin
7-OH-PIPAT = 7-Hydroxy-2-[N-3'-(1'-Iodo-1'E-Propenyl)-N-n-Propyl-amino]tetralin c. Discussion of Results The ability of a ligand of this invention, 7-OH-PIPAT, to inhibit [$^{125}$I]-NCQ 298 in Sf9 cell lines expressing either D2 or D3 dopamine receptors was compared to the same ability of numerous structurally related compounds (7-MeO-MPAT, 7-OH-MPAT, 7-MeO-DPAT, 7-OH-DPAT, 8-I-7-OH-DPAT, 7-Meo-BAT, 7-OH-BAT, and 7-OH-PPAT). The selectivity of each ligand was expressed by the ratio: Ki(D2)/Ki(D3).

All of the ligands derivatives displayed a higher affinity for D3 receptors than for D2 receptors (Ki(D2)>Ki(D3)). All free hydroxylated derivatives exhibited more affinity for either D2 or D3 receptors than their methoxylated analogs. The mono-propylaminotetralin (7-OH-MPAT) displayed a comparative affinity as 7-OH-DPAT for D3 receptors but turned out to be much more selective (ratio D2/D3=191). Among all the hydroxylated compounds, the benzyl derivative (7-OH-BAT) exhibited the lowest affinity for the D3 receptor. Although not intending to be bound by any theory, it is believed that the large size of the benzyl ring as well as its proximity to the nitrogen might prevent this latter from binding to the receptor or might introduce some distortions in the molecule that change its optimal configuration.

The presence of the propargyl function on the nitrogen induced a restriction of the conformation due to the linear position of the two carbons involved in the triple bond. This combination did not seem to be fitted by the receptor as well as the propyl chain: (7-OH-PPAT) is three-fold less active than 7-OH-DPAT for either D2 (Ki(8)=378 nM; Ki(7)=142 nM) or D3 receptors (Ki(8)=9.2 nM; Ki(7)=2.9 nM).

The introduction of an iodine on the alpha position of the hydroxyl function of the aromatic ring (8-I-7-OH-DPAT) led to a dramatic decrease of the affinity for D3 receptors (Ki(7-OH-DPAT) =2.9 nM; Ki(8-I-7-OH-DPAT)=21.3 nM) as well as the lost of selectivity (ratio(7)=48.9; ratio(9)= 16.6). Again, not intending to be bound by any theory, it is thought that this poor result can be explained by the big size of the halogen which might "mask" the hydroxyl from the binding site. The low affinity displayed by the methoxylated derivatives coupled with the loss of activity of the iodinated 7-OH-DPAT underlined clearly the fundamental role of the hydroxyl function to the binding to the dopamine receptor.

The ligands 7-MeO-PIPAT and 7-OH-PIPAT incorporate the halogen as a iodopropenyl substituent of the nitrogen. 7-MeO-PIPAT displayed a low affinity (Ki=257 nM) whereas 7-OH-PIPAT exhibited a high affinity (Ki=1.85 nM) and selectivity (Ratio=143) for the D3 receptor. Compared with 7-OH-PIPAT, not only the affinity for the D3 receptor was improved but the selectivity as well (Ki(7-OH-DPAT) =2.9; ratio(7-OH-DPAT)=48.9).

These results show clearly the importance of the hydroxylated function on the phenyl ring for the binding to the D3 receptor. It seems also that the presence of at least one propyl on the nitrogen is another necessary element. The high affinity of 7-OH-PIPAT for the D3 receptor as well its high selectivity should make this ligand a powerful tool for the visualization of the D3 receptors by autoradiography.

EXAMPLE 5

In-vivo biodistribution of 7-OH-PIPAT in rats

In-vivo biodistribution studies were performed in rats[27] with the two hydroxylated radioligands: [$^{123}$I]-7-OH-DPAT and [$^{123}$I]-7-OH-PIPAT in rats. Concerning [$^{123}$I]-7-OH-DPAT rats were killed either two minutes or thirty minutes post injection and the data are reported in Table 5. The radioligand was rapidly washed out of the brain and no regional uptake was observed in the different area of the brain. On the contrary, [$^{123}$I]-7-OH-PIPAT presented a very high brain uptake: 11.812, 9.458 and 5.433% dose/gram of tissue at 2, 30 and 60 min. respectively (See Table 6). Unfortunately, no regional uptake was observed in the different area of the brain. However, the brain regions, rich in D3 receptors such as Calleja island and olfactory tubercle need to be more deeply investigated.

TABLE 5

IN VIVO BIODISTRIBUTION OF [$^{123}$I]-7-OH-DPAT IN RATS

| Organ | 2 min. | 30 min. |
|---|---|---|
| Blood | 3.40 ± 0.18 | 1.78 ± 0.26 |
| Heart | 0.93 ± 0.09 | 0.15 ± 0.03 |
| Muscle | 19.27 ± 5.28 | 11.85 ± 3.02 |
| Lung | 7.42 ± 1.31 | 1.47 ± 0.08 |
| Kidney | 6.90 ± 0.82 | 2.34 ± 0.55 |
| Spleen | 0.60 ± 0.10 | 0.35 ± 0.11 |
| Liver | 9.02 ± 1.61 | 3.60 ± 1.11 |
| Skin | 6.19 ± 0.89 | 8.50 ± 0.23 |
| Thyroid | 0.08 ± 0.02 | 0.06 ± 0.03 |
| Brain | 1.55 ± 0.21 | 0.54 ± 0.13 |
| Regional uptake (% dose/g) | | |
| Cerebellum | 0.81 ± 0.14 | 0.25 ± 0.09 |
| Striatum | 0.85 ± 0.07 | 0.31 ± 0.08 |
| Hippocampus | 0.78 ± 0.09 | 0.31 ± 0.07 |
| Cortex | 1.10 ± 0.12 | 0.29 ± 0.12 |

TABLE 6

IN VIVO BIODISTRIBUTION OF [$^{123}$I]-7-OH-PIPAT IN RATS

| Organ min. (c) | 2 min. (a) | 30 min. (b) | 60 min. (c) |
|---|---|---|---|
| Blood | 2.621 ± 0.298 | 0.785 ± 0.089 | 0.742 ± 0.075 |
| Heart | 1.780 ± 0.231 | 0.203 ± 0.054 | 0.100 ± 0.010 |
| Muscle | 33.199 ± 11.64 | 23.546 ± 8.469 | 12.882 ± 3.927 |
| Lung | 5.394 ± 0.589 | 0.768 ± 0.146 | 0.437 ± 0.038 |
| Kidney | 5.887 ± 1.088 | 0.978 ± 0.276 | 1.042 ± 0.114 |
| Spleen | 0.449 ± 0.161 | 0.284 ± 0.011 | 0.180 ± 0.023 |
| Liver | 9.687 ± 3.302 | 3.573 ± 0.569 | 2.335 ± 1.391 |

TABLE 6-continued

IN VIVO BIODISTRIBUTION OF [$^{123}$I]-7-OH-PIPAT IN RATS

| Organ min. (c) | 2 min. (a) | 30 min. (b) | 60 min. (c) |
|---|---|---|---|
| Skin | 8.816 ± 1.656 | 6.962 ± 0.362 | 6.148 ± 0.922 |
| Thyroid | 0.174 ± 0.012 | 0.045 ± 0.007 | 0.096 ± 0.067 |
| Brain | 2.612 ± 0.498 | 0.660 ± 0.096 | 0.321 ± 0.037 |
| Regional uptake (% dose/g) | | | |
| Cerebellum | 1.613 ± 0.403 | 0.379 ± 0.009 | 0.215 ± 0.025 |
| Hypothalamus | 1.835 ± 0.233 | 0.251 ± 0.009 | 0.254 ± 0.033 |
| Striatum | 1.618 ± 0.236 | 0.263 ± 0.080 | 0.212 ± 0.029 |
| Hippocampus | 1.631 ± 0.222 | 0.261 ± 0.064 | 0.216 ± 0.020 |
| Cortex | 1.998 ± 0.038 | 0.265 ± 0.086 | 0.206 ± 0.022 |
| REM | 1.665 ± 0.224 | 0.281 ± 0.076 | 0.218 ± 0.025 |

EXAMPLE 6

Preparation of (R,S)-2'-trans-8-hydroxy-2-[N-(3'-iodo-2'-propenyl)-N-n-propyl]aminotetralin (trans-8-OH-PIPAT)

a. 8-Methoxy-2-(N-2'-propynyl)aminotetralin(3):

The mixture of 8-methoxy-2-tetralone (2, 2.5 g, 14.2 mmole) prepared from 1,7-dihydroxy naphthalene in two steps, 2-propynylamine (3.9 g, 4.9 ml, 5 eq.) and p-TsOH (150 mg, 0.8 mmole) in benzene (30 mL), was refluxed with a Dean-Stark trap for two hours. The solvent was removed on a rotavapor after cooling. The residue was dissolved in MeOH (30 mL), to which NaCNBH$_3$ (540 mg, 8.7 mmole) was added in solid form. The solution was stirred at room temperature for 30 minutes and acidified with HCl (10%) to pH 1. The mixture was extracted with ether to remove neutral impurity and the aqueous phase was alkalized first with NaHCO$_3$ then with NaOH (1M) to pH>8. The mixture was extracted with CH$_2$Cl$_2$. After condensation, the dark oil was purified by flash chromatography (eluent: CH$_2$Cl$_2$: MeOH=96:4) to give the product (1.96 g) in 64% yield. IR(film, v$_{max}$): 3300, 3000, 2900, 2200, 1620, 1600, 1250 cm$^{-1}$. $^1$H NMR (CDCl$_3$, δppm): 1.57, 1.61 (1H, dt, J=10.3, 6.2 Hz, NHCHCH$_a$H$_b$CH$_2$), 1.71 (1H, br, NH), 2.01 (1H, m, NHCHCH$_a$H$_b$CH$_2$), 2.21 (1H, t, J=2.3 Hz, propynyl), 2.33 (1H, dd, J=16.6, 9.1 Hz, ArCH$_a$H$_b$CHN), 2.84 (2H, m, ArCH$_2$CH$_2$CHN), 3.05 (1H, dd, J=16.6, 4.8 Hz, ArCH$_a$H$_b$CHN), 3.18 (1H, m, NCH), 3.58 (2H, d, J=2.4 Hz, NHCH$_2$), 3.80 (3H, s, OCH$_3$), 6.66 (1H, d, J=8.1 Hz, Ar—H), 6.72 (1H, d, J=7.8 Hz, Ar—H), 7.09 (1H, t, J=7.9 Hz, Ar—H).

MS: M/Z 216 (M$^+$+1), 200, 161, 134, 115.

Elemental Anal. (C$_{14}$H$_{17}$ON·HCl·¼H$_2$O): C,H,N.

b. trans-8-Methoxy-2-(N-3'-tributylstannyl-2'-propenyl)aminotetralin(4):

A mixture of 3 (200 mg, 0.93 mmol), HSnBu$_3$ (650 mg, 0.6 mL, 2.2 mmole, 2.5 eq) and AIBN (32 mg, 0.2 mmole) in toluene (5 mL) was stirred at 105° C. under uN$_2$ for four hours. The solvent was removed on the rotavapor after cooling and the residue was purified by flash chromatography (eluent: Hexene: EtOAc=3:1) to give 4 as a yellow oil (402 mg) in 85% yield. IR (film, v$_{max}$): 3000, 1620, 1600, 1450, 1250 cm$^{-1}$. $^1$H NMR (CDCl$_3$, δppm): 0.88 (15H, t, J=7.3 Hz, CH$_3$, SnCH$_2$), 1.30 (6H, hex, J=7.1 Hz, CH$_3$C H$_2$), 1.50 (6H, m, CH$_3$CH$_2$CH$_2$), 1.6 (2H, m, ArCH$_2$C H$_2$CHN), 2.05 (1H, m, NH), 2.36 (1H, dd, J=16.7, 9.2 HZ, ArCH$_a$H$_b$CHN), 2.88 (2H, m, ArCH$_2$CH$_2$CHN), 2.98 (1H, m, NCH), 3.10 (1H, dd, J=16.8, 5.1 Hz, ArCH$_a$H$_b$CHN), 3.46 (2H, d, J=3.7 Hz, NHC$\underline{H}_2$), 3.81 (3H, s, OC$\underline{H}_3$), 6.09 (1H, dt, J=18.9, 4.0 Hz, C$\underline{H}$=CHSn), 6.16 (1H, d, J=18.9 Hz, CH=C$\underline{H}$Sn), 6.66 (1H, d, J=8.0 Hz, Ar—$\underline{H}$), 6.72 (1H, d, J=7.7 Hz, Ar—$\underline{H}$), 7.09 (1H, t, J=7.9 Hz, Ar—$\underline{H}$).

MS: M/Z 508 (M$^+$+1), 450, 392.

Elemental Anal. (C$_{26}$H$_{45}$ONSn): C.H.N.

c. 8-Methoxy-2-(N-3'-iodo-2'-propenyl) aminotetralin (5):

To a solution of starting material (4, 260 mg, 0.51 mmole) in CHCl$_3$ (20 mL) was added iodine (0.1M solution in CHCl$_3$) dropwise at room temperature until an iodine color persisted. The mixture was stirred at room temperature overnight. KF (6 mL, 1M in MeOH) and KHSO$_3$ (6 mL, 5% aqueous solution) were added, and the mixture was stirred at room temperature for 30 minutes and extracted with CH$_2$Cl$_2$. After condensation, the crude product was purified by flash chromatography (eluent: Hexene: EtOAc=3:1) to give 145 mg of product (82% yield). Separation with preparative thin layer chromatography (PTCL) gave trans and cis isomers in 2:1 ratio.

IR (film, v$_{max}$): 2950, 2850, 1620, 1600, 1450, 1420, 1300 1250 cm$^{-1}$. $^1$H NMR (CDCl$_3$, δ) trans isomer: 1.48, 1.52 (1H, dt, J=10.1, 6.1 Hz, CH$_2$C$\underline{H}_a$H$_b$CHN), 1.70 (1H, m, N$\underline{H}$), 1.93 (1H, m, CH$_2$CH$_a$$\underline{H}_b$CHN), 2.25 (1H, dd, J=16.6, 8.9 Hz ArC$\underline{H}_a$H$_b$CHN) , 2.76 (2H, m, ArC$\underline{H}_2$CH$_2$CHN), 2.87 (1H, m, C$\underline{H}$N), 2.98 (1H, dd, J=16.8, 4.8 Hz, ArCH$_a$$\underline{H}_b$CHN), 3.30 (2H, d, J=6.4 Hz, NC$\underline{H}_2$), 3.74 (3H, s, OC$\underline{H}_3$), 6.22 (1H, dt, J=14.5, 1.2 Hz, CH=C$\underline{H}$I), 6.58 (dt, J=14.5, 6.2 Hz, C$\underline{H}$=CHI), 6.59 (1H, d, J=8.1 Hz, Ar—$\underline{H}$), 6.67 (1H, d, J=7.4 Hz, Ar—$\underline{H}$), 7.02 (1H, t, J=7.9 Hz, Ar—$\underline{H}$). cis isomer: 1.51, 1.56 (1H, dt, J=10.2, 5.9 Hz, CH$_2$C$\underline{H}_a$H$_b$CHN), 2.02 (1H, m, CH$_2$CH$_a$$\underline{H}_b$CHN), 2.19 (1H, m, N$\underline{H}$), 2.25 (1H, dd, J=16.7, 9.0 Hz, ArC$\underline{H}_a$H$_b$CHN), 2.78 (2H, m, ArC$\underline{H}_2$CH$_2$CHN), 2.88 (1H, m, C$\underline{H}$N), 3.03 (1H, dd, J=16.6, 5.0 Hz, ArCH$_a$$\underline{H}_b$CHN), 3.43 (2H, d, J=5.8 Hz, NC$\underline{H}_2$), 3.73 (3H, s, OC$\underline{H}_3$), 6.28 (1H, dt, J=7.5, 1.4 Hz, CH=C$\underline{H}$I), 6.33 (dt, J=7.5, 5.7 Hz, C$\underline{H}$+CHI), 6.58 (1H, d, J=8.1 Hz, Ar—$\underline{H}$), 6.63 (1H, d, J=7.6 Hz, Ar—$\underline{H}$), 7.01 (1H, t, J=7.9 Hz, Ar—$\underline{H}$).

MS: M/Z 344 (M$^+$+1) 216, 212, 161.

Elemental Anal. (C$_{14}$H$_{18}$ONI·HCl): C.H.N.

d. 8-Hydroxy-2-(N-3'-iodo-2'propenyl)aminotetralin (6):

To a solution of the iodinated 5 (60 mg, 0.17 mmole) in CH$_2$Cl$_2$ (5 mL) was added BBR$_3$ (1 mL, 1M in CH$_2$Cl$_2$, 5 eq) dropwise at −78° C. in a dry ice-acetone bath. After completion of the addition, the cold bath was removed and the mixture was stirred at room temperature overnight. Ice water (5 mL) was added. The mixture was stirred at room temperature for 30 minutes and extracted with CH$_2$Cl$_2$. The aqueous phase was filtered and the filtrate was alkalized to pH about 7–8, white solid precipitated and the whole mixture was extracted with CH$_2$Cl$_2$—MeOH (96:4). The organic layer was dried and evaporated to give a crude product which was purified by PTLC (CH$_2$Cl$_2$:MeOH=96:4 as solvent) to give 23 mg of product (40% yield).

IR (film, v$_{max}$): 3300, 2900, 2850, 1620, 1600, 1450, 1350, 1250 cm$^{-1}$.

$^1$H NMR (CDCl$_3$, δ) trans isomer: 1.17 (1H, br, N$\underline{H}$), 1.46, 1.50 (1H, dt, J=10.2, 6.5 Hz, CH$_2$C$\underline{H}_a$H$_b$CHN), 1.96 (1H, m, CH$_2$CH$_a$$\underline{H}_b$CHN), 2.25 (1H, dd, J=16.2, 9.4 Hz, ArC$\underline{H}_a$H$_b$CHN) , 2.73 (2H, m, ArC$\underline{H}_2$CH$_2$CHN), 2.90 (1H, m, C$\underline{H}$N), 3.00 (1H, dd, J=16.4, 5.0 Hz, ArCH$_a$$\underline{H}_b$CHN), 3.28 (2H, d, J=6.8 Hz, NC$\underline{H}_2$), 6.32 (1H, d, J=14.6 Hz, CH=C$\underline{H}$I), 6.52 (2H, d, J=7.7 Hz, Ar—$\underline{H}$), 6.56 (1H, dt, J=14.8, 6.5 Hz, C$\underline{H}$=CHI), 6.87 (1H, t, J=7.7 Hz, Ar—$\underline{H}$).

MS: M/Z 330 (M$^+$+1), 202, 162, 146, 120.

Elemental Anal. (C$_{13}$H$_{16}$ONI): C.H.N.

e. trans-8-Methoxy-2-[N-propyl-N-(3'-iodo-2'propenyl)] aminotetralin (7):

The mixture of starting material, 5 (145 mg, 0.42 mmole), 1-iodopropane (1 g, 0.6 mL, 5.9 mmole) and K$_2$CO$_3$ (0.3 g, 2.2 mmole) in EtOH (6 mL) was refluxed under N$_2$ for 40 hours. The solvent was removed and the residue was purified by flash chromatography (eluent: CH$_2$Cl$_2$:MeOH=96:4) to give 130 mg of product (80% yield) Only the trans isomer was isolated.

IR (film, v$_{max}$): 2900, 2800, 1620, 1600, 1450, 1400, 1250 cm$^{-1}$. $^1$H NMR (CDCl$_3$, δ) 0.82 (3H, t, J=7.4 Hz, C$\underline{H}_3$), 1.39 (2H, hex, J=7.4 Hz, C$\underline{H}_2$CH$_3$), 1.50–2.78 (9H, m, —C$\underline{H}_2$—, C$\underline{H}$N), 3.12 (2H, d, J=6.2 Hz, NC$\underline{H}_2$), 3.75 (3H, s, OC$\underline{H}_3$), 6.15 (1H, d, J=14.4 Hz, CH=C$\underline{H}$I), 6.53 (1H, dt, J=14.3, 6.3 Hz, C$\underline{H}$=CHI), 6.59 (1H, d, J=8.4 Hz, Ar—$\underline{H}$), 6.63 (1H, d, J=7.7 Hz, Ar—$\underline{H}$), 7.01 (1H, t, J=7.9 Hz, Ar—$\underline{H}$).

MS: M/Z 385 (M$^+$), 355, 258, 228, 161, 122.

Elemental Anal. (C$_{17}$H$_{24}$ONI·HCl): C.H.N.

f. trans-8-Hydroxy-2-[N-propyl-N-(3'-iodo-2'propenyl)] aminotetralin (8):

To a solution of starting material, 7 (120 mg, 0.31 mmole), in CH$_2$Cl$_2$ (10 mL) was added BBr$_3$ (1.3 mL, 1M in CH$_2$Cl$_2$, 4 eq) dropwise at −78° C. in a dry ice-acetone bath. The cold bath was removed and the mixture was stirred at room temperature overnight. Ice water (10 mL) was added and the mixture was stirred at room temperature for 30 minutes. The organic phase was separated, dried and evaporated to give a crude product which was purified by PTLC (CH$_2$Cl$_2$: MeOH=96:4 as solvent) to give 88 mg of product (76% yield).

IR (film, v$_{max}$): 3400, 3100, 3000, 1620, 1600, 1450, 1300, 1250 cm$^{-1}$. $^1$H NMR (CDCl$_3$, δ): 0.82 (3H, t, J=7.4 Hz, C$\underline{H}_3$), 1.41 (2H, hex, J=7.4 Hz, C$\underline{H}_2$CH$_3$), 1.48–2.98 (9H, m, —C$\underline{H}_2$—, C$\underline{H}$N), 3.15 (2H, d, J=6.3 Hz, NC$\underline{H}_2$), 6.19 (1H, d, J=14.4 Hz, CH=C$\underline{H}$I), 6.53 (1H, dt, J=14.3, 5.3 Hz, C$\underline{H}$=CHI), 6.54 (1H, d, J=8.1 Hz, Ar—$\underline{H}$), 6.61 (1H, d, J=7.6 Hz, Ar—$\underline{H}$), 6.92 (1H, t, J=7.8 Hz, Ar—$\underline{H}$).

MS: M/Z 372 (M$^+$+1), 341, 244, 147.

Elemental Anal. (C$_{16}$H$_{22}$ONI·HCl): C.H.N.

f. 8-Methoxy-2-(N-propyl-N-2'-propynyl)aminotetralin (9):

The mixture of starting material, 3 (500 mg, 2.33 mmole), 1-iodopropane (3.5 g, 2 mL, 20.5 mmole) and K$_2$CO$_3$ (1 g, 7.2 mmole) in EtOH (10 mL) was refluxed under N$_2$ for 18 hours. The solvent was removed and the residue was purified by flash chromatography (eluent: Hexene: EtOAc=1:6) to give 520 mg of product (87% yield).

IR (film, v$_{max}$): 3300, 3000, 2800, 2200, 1620, 1600, 1450, 1420, 1300, 1300, 1250 cm$^{-1}$. $^1$H NMR (CDCl$_3$, δ): 0.94 (3H, t, J=7.4 Hz, C$\underline{H}_3$) 1.57 (2H, m, CH$_3$C$\underline{H}_2$), 1.60–2.16 (2H, m, CH$_2$C$\underline{H}_2$CHN), 2.18 (1H, t, J=2.3 Hz, propynyl), 2.47 (1H, dd, J=16.6, 10.4, ArC$\underline{H}_a$H$_b$CHN), 2.66 (2H, t, J=7.5 Hz, NC$\underline{H}_2$CH$_2$CH$_3$), 2.83 −3.01 (3H, m, ArC$\underline{H}_2$CH$_2$CHN) , C$\underline{H}$N), 3.08 (1H, dd, J=16.6, 4.9 Hz, ArCH$_a$$\underline{H}_b$CHN), 3.56 (2H, d, J=2.3 Hz, NC$\underline{H}_2$), 3.82 (3H, s, OC$\underline{H}_3$), 6.66 (1H, d, J=8.1 Hz, Ar—$\underline{H}$), 6.71 (1H, d, J=7.5 Hz, Ar—$\underline{H}$), 7.09 (1H, t, J=7.9 Hz, Ar—$\underline{H}$).

MS: M/Z 257 (M$^+$), 242, 228, 161, 122

Elemental Anal. (C$_{17}$H$_{23}$ON.HCl.¼ H$_2$O): C.H.N.

g. 8-Hydroxy-2-(N-propyl-N-2'-propynyl) aminotetralin (10):

To a solution of starting material, 9 (460 mg, 1.79 mmole), in CH$_2$Cl$_2$ (30 mL) was added BBr$_3$ (7.5 mL, 1M in CH$_2$Cl$_2$, 4 eq) dropwise at −78° C. in a dry ice-acetone bath under N$_2$. The cold bath was removed and the mixture was stirred at room temperature overnight. Ice water (20 mL) was added and the mixture was stirred at room temperature for 10 minutes, alkalized with NaOH (1M) to pH about 8 and extracted with CH₂Cl₂. Work up gave a crude product which was purified by flash chromatography (eluent: CH₂CL₂: MeOH=96:4) to give 385 mg of product (89% yield).

IR (film, $v_{max}$): 3300, 3050, 2950, 2200, 1600, 1450, 1400, 1300, 1270 cm⁻¹. ¹H NMR (CDCl3, δ): 0.93 (3H, t, J=7.4 Hz, CH₃), 1.47–2.18 (4H, m, —CH₂—), 2.19 (1H, t, J=2.3 Hz, propynyl), 2.49–3.08 (7H, m, CH₂, CHN), 3.57 (2H, d, J=1.9 Hz, NCH₂), 6.59 (1H, d, J=7.9 Hz, Ar—H), 6.68 (1H, d, J=7.6 Hz, Ar—H), 6.99 (1H, t, J=7.7 Hz, Ar—H).

MS: M/Z (M⁺), 228, 214, 147.

Elemental Anal. (C₁₆H₂₁ON.HCl.1/4 H₂O): C.H.N.

h. trans-8-Hydroxy-2-(N-propyl-N-3'-tributylstannyl-2'-propenyl)aminotetralin (11):

The mixture of starting material, 10 (90 mg, 0.37 mmol), HSnBu₃ (325 mg, 0.3 mL, 1.1 mmole, 3 eq) and AIBN (24 mg, 0.15 mmole) in toluene (10 mL) was stirred at 105° C. under N₂ for 3 hours. The solvent was removed on the rotavapor after cooling and the residue was purified by PTLC to give an oil (95 mg) in 48% yield. Only the trans isomer was isolated.

IR (film, $v_{max}$): 3400, 2970, 2920, 2850, 1600, 1350, 1300, 1250 cm⁻¹. ¹H NMR (CDCl3, δ): 0.87 (9H, t, J=7.2 Hz, CH₃), 0.84–0.92 (9H, m, SnCH₂, CH₃CH₂), 1.21–2.86 (23 H, m, —CH₂—, CHN, CH₂N), 3.31 (2H, t, J=4.3 Hz, NCH₂), 6.04 (1H, dt, J=18.8, 4.8 Hz, CH₂CH=CHSn), 6.13 (1H, d, J=18.9 Hz, CH=CHSn), 6.60 (1H, d, J=7.9 Hz, Ar—H), 6.67 (1H, d, J=7.8 Hz, Ar—H), 6.98 (1H, t, J=7.7 Hz, Ar—H).

MS: M/Z 536 (M⁺+1), 478, 391, 332, 246.

Elemental Anal. (C₂₈H₁₉ONSn): C.H.N.

i. Preparation of [¹²⁵I] trans-8-OH-PIPAT(¹²⁵I])

No-carrier-added [¹²⁵I ]trans-8-OH-PIPAT(¹²⁵I]8) was prepared by an iododestannylation reaction similar to the procedure reported previously (Acta. Chim. Scan., 1988, B42, 231–236). Hydrogen peroxide (50 μl 3% w/v) was added to a mixture of 50 μl of tributyltin precursor, 11 (11 mg/ml EtOH), 50 μl of 1N HCl and I-125 (2–3 mCi) in a sealed vial. The reaction was allowed to proceed for 20 minutes at room temperature, and was then terminated by addition of 0.1 ml of sodium bisulfite (300 mg/ml). The reaction mixture was extracted with ethyl acetate (3×1 ml) after neutralization with saturated NaHCO₃ solution. The extracted ethyl acetate layers were evaporated to dryness, and the remaining residue was dissolved in EtOH and purified by HPCL using a reverse phase column (PRP-1 column, Hamilton Co., Reno, Nev.) eluted with an isocratic solvent of 80% acetonitrile-20% pH 7.0 buffer (5 mM 3,3'-dimethylglutaric acid); the retention time was 9 minutes (1 ml/min). The fractions containing the desired product were collected, condensed and re-extracted with ethyl acetate (3×1 ml). The final product of no-carrier-added (purity>98%) was evaporated to dryness and redissolved in 100 μl of 50% EtOH with 100 μg of ascorbic acid added as an anti-oxidant. The final product [¹²⁵I] trans-8-OH-PIPAT (¹²⁵I]8) was stored at –20° C. The stability of the product was evaluated from three preparations and was found to be stable for at least four weeks (95% pure, analyzed by HPCL).

| Compound | Elemental Analysis | | | | | |
|---|---|---|---|---|---|---|
| | Calculated (%) | | | Found (%) | | |
| | C | H | N | C | H | N |
| (3) C₁₄H₁₇ON.HCl.½H₂O | 65.62 | 7.22 | 5.46 | 65.71 | 7.26 | 5.48 |
| (4) C₂₆H₄₅ONSn | 61.51 | 8.94 | 2.76 | 61.56 | 8.98 | 2.73 |
| (5) C₁₄H₁₈ONl.HCl | 44.29 | 5.04 | 3.69 | 44.35 | 5.11 | 3.60 |
| (6) C₁₃H₁₆ONI | 47.41 | 4.90 | 4.26 | 47.18 | 4.94 | 4.17 |
| (7) C₁₇H₂₄ONl.HCl | 48.41 | 5.97 | 3.32 | 48.53 | 6.00 | 3.24 |
| (8) C₁₆H₂₂ONl.HCl | 47.13 | 5.69 | 3.44 | 47.04 | 5.71 | 3.41 |
| (9) C₁₇H₂₃ON.HCl.½H₂O | 68.45 | 8.22 | 4.69 | 68.46 | 8.29 | 4.68 |
| (10) C₁₆H₂₁ON.HCl.½H₂O | 67.60 | 7.92 | 4.93 | 67.62 | 8.03 | 4.88 |
| (11) C₂₈H₄₉ONSn | 62.93 | 9.24 | 2.62 | 62.75 | 9.28 | 2.60 |

EXAMPLE 7

Biological Activity of 8-OH-PIPAT

Figure 2A:
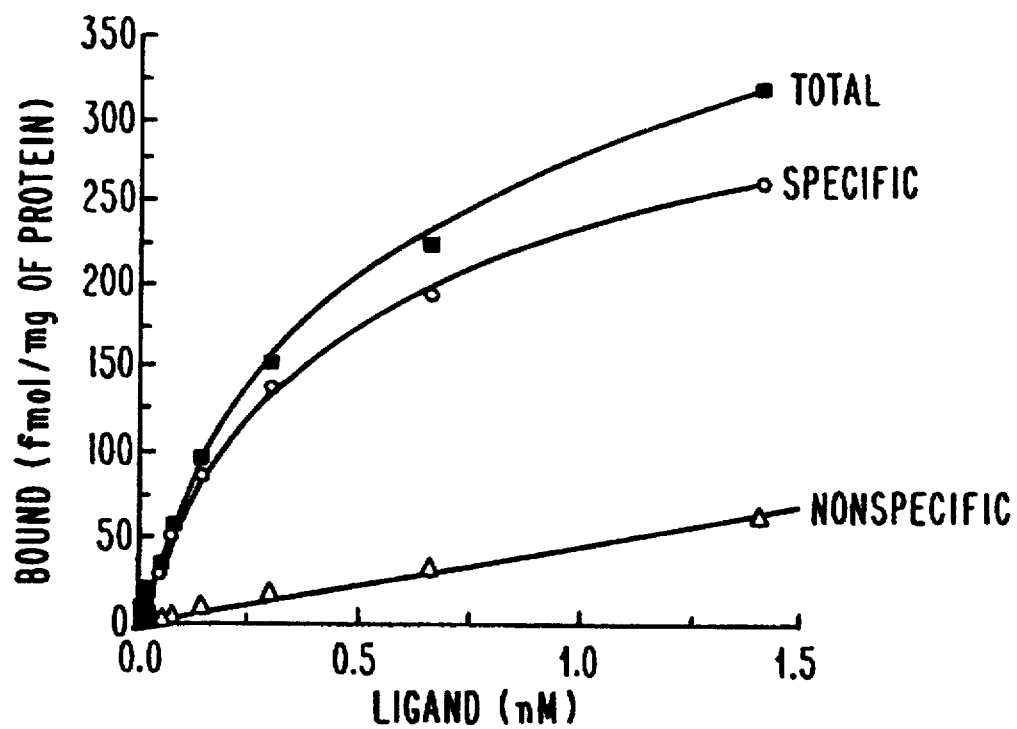
FIGS. 2A and 2B comprise saturation and scatchard plots of binding of [$^{125}$I]trans-8-OH-PIPAT in rat hippocampal membrane preparations.
Figure 2B:
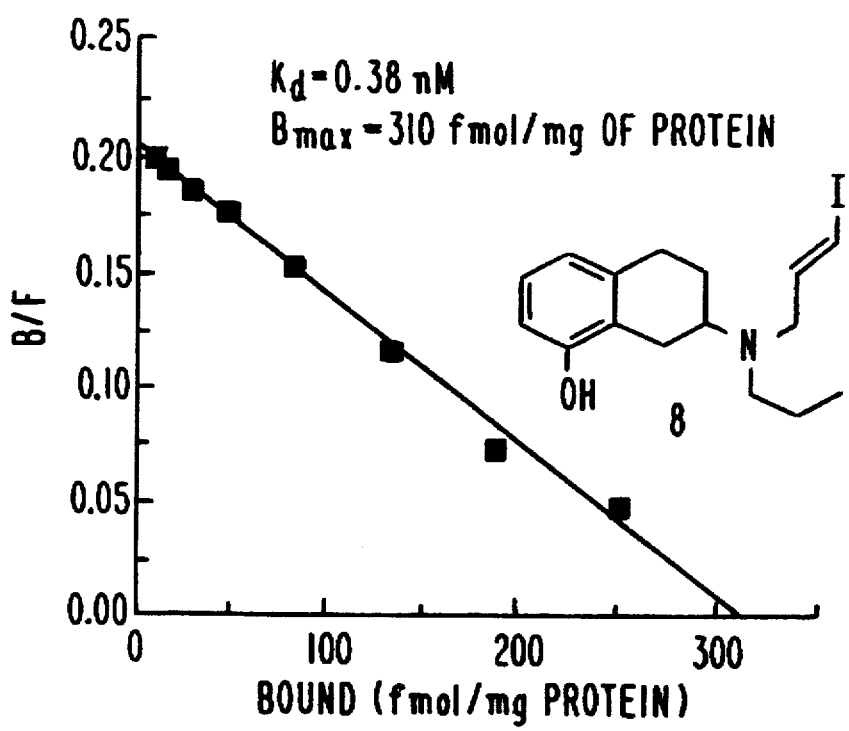

Binding studies with rat hippocampal membrane preparations were carried out using 8-OH-PIPAT and structurally related ligands, with the results presented below in Table 7 and in FIG. 2.

The hippocampal homogenates were prepared in 100 volumes of ice-cold Tris-HCl buffer (50mM, pH 7.4) and centrifuged at 20,000 g for 20 minutes. The resulting pellets were resuspended in ice-cold water to lyse vesicules, and subsequently preincubated at 37° C. and recentrifugated to remove the endogenous serotonin. The final pellets were resuspended in the Tris-buffer containing 2mM of MgCl₂. The binding assays were carried out in a total volume of 0.2 ml containing 50μl of tissue preparations (40–60 μg protein), various amounts of radioligands (for saturation experiments) or appropriate amounts of labeled ligand (0.2–0.4 mM) and different concentrations of inhibitors (for competition experiments). The tubes were incubated at 37° C. for fifteen minutes and then terminated by vacuum filtration through glass filters (Schleicher & Schuell, No. 25, Keene, N.H.) soaked with 1% polyethylimine. The filters were then washed twice with 4 ml ice-cold buffer and the radioactivity on the filters was counted in a gamma counter (Packard 5000). Nonspecific binding was defined with 10 μM 5-HT. Both Scatchard and competition experiments were analyzed using the iterative least-square curve fitting program LIGAND.

TABLE 7

Inhibition Constants of 8-OH-DPAT and Derivatives on Binding of [³H]-8-OH-DPAT to Hippocamus Membrane Homogenates of Rat Brain

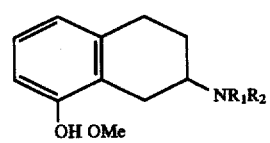

| Ligand | R₁ | R₂ | K₁ (nM) |
|---|---|---|---|
| (±)trans-8-OH-DPAT | n-Pr | nPr | 0.63 ± 0.12 |
| (±)trans-8-OH-PIPAT | n-Pr | CH₂CH=CHI | 0.92 ± 0.13 |
| (±)trans-8-OMe-PIPAT | n-Pr | CH₂CH=CHI | 12.6 ± 1.5 |
| (±)trans-8-OH-IPAT | H | CH₂CH=CHI | 10 ± 2 |
| (±)trans-8-OMe-IPAT | H | CH₂CH=CHI | 17 ± 2.2 |

The results reported in Table 7 suggest that the ligand 8-OH-PIPAT is an excellent analog showing a Ki value of 0.92 nM against ³H-8-OH-DPAT. These results also suggest that the 5-HT1a binding requires the presence of at least one n-propyl group and a free 8-OH group.

What is claimed is:

1. Compounds of the formula

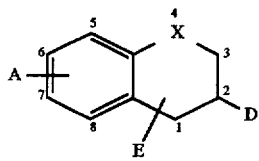

where

A is selected from the group consisting of OH and OCH$_3$ and is at the 7- or 8-ring position;

X is selected from the group consisting of CH$_2$, O and S;

D is —N(CH$_2$CH$_2$CH$_3$)(R);

R is selected from the group consisting of H, C$_1$–C$_5$ alkyl and (CH$_2$)$_n$CH=CHR';

n is 1 or 2;

R' is selected from the group consisting of an iodine atom, a bromine atom, a methyl group and an ethyl group;

E is selected from the group consisting of H, C$_1$–C$_5$ alkyl and (CH$_2$)$_n$CH=CHR' and is at the 1- or 3-ring position;

provided that one of D and E contains the moiety (CH$_2$)$_n$CH=CHR' wherein R' is selected from the group consisting of an iodine atom and a bromine atom;

or D and E may be taken together to form a ring selected from the group consisting of

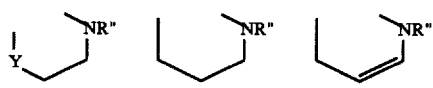

where

R" is (CH$_2$)$_n$CH=CH—R', provided that R' is here selected from the group consisting of an iodine atom and a bromine atom; and Y is selected from the group consisting of CH$_2$, O and S;

provided that such compound is an R-isomer;

and pharmaceutically acceptable salts thereof.

2. A compound of claim 1 where A is OH.
3. A compound of claim 2 where A is in the 7-position.
4. A compound of claim 2 where A is in the 8-position.
5. A compound of claim 1 where X is CH$_2$.
6. A compound of claim 2 where D is N(propyl)(R) and R is (CH$_2$)$_n$CH=CHR'.
7. A compound of claim 6 n is 1.
8. A compound of claim 6 where R' is selected from the group consisting of an iodine atom and a bromine atom.
9. A compound of claim 8 where R' is an iodine atom.
10. A compound of claim 9 where the iodine atom is a radioactive isotope.
11. A compound of claim 1 where E is H.
12. A compound of claim 3 where X is CH$_2$, D is N(Propyl)(R), and R is (CH$_2$)$_n$CH=CHR'.
13. A compound of claim 12 were n is 1 and R' is an iodine atom.
14. A compound of claim 13 where E is N.
15. A compound of claim 4 where X is CH$_2$, D is N(Propyl)(R), and R is (CH$_2$)$_n$CH=CHR'.
16. A compound of claim 15 were n is 1 and R' is an iodine atom.
17. A compound of claim 16 where E is H.
18. The compound of claim 14 which is 7-hydroxy-2-(N-n-propyl-N-3'-iodo-2'-propenyl)-amino]tetralin.
19. The compound of claim 17 which is 8-hydroxy-2-(N-n-propyl-N-3'-iodo-2'-propenyl)amino-tetralin.
20. Compounds of the formula

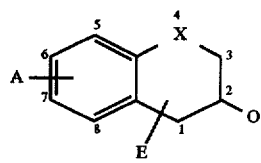

where

A is selected from the group consisting of OH and OCH$_3$ and is at the 7- or 8-ring position;

X is selected from the group consisting of CH$_2$, O and S;

D is —N(CH$_2$CH$_2$CH$_3$)(R$_1$);

R$_1$ is selected from the group consisting of H, C$_1$–C$_5$ alkyl and (CH$_2$)$_n$CH=CHSnBu$_3$;

n is 1 or 2;

E is selected from the group consisting of H, C$_1$–C$_5$ alkyl and (CH$_2$)$_n$CH=CHSnBu$_3$ and is at the 1- or 3- ring position;

provided that one of D and E contains the moiety (CH$_2$)$_n$CH=CHSnBu$_3$;

or D and E may be taken together to form a ring selected from the group consisting of

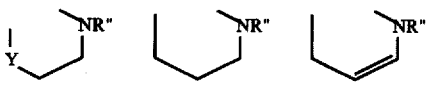

where

R" is (CH$_2$)$_n$CH=CH—SnBu$_3$; and

Y is selected from the group consisting of CH$_2$, O and S; provided that such compound is an R-isomer.

21. Compounds of claim 20 where X is CH$_2$.
22. Compounds of claim 20 where A is OH.
23. Compounds of claim 20 where E is H.
24. Compounds of claim 20 where X is CH$_2$, A is OH, and E is H.
25. A dopamine receptor imaging agent comprising a compound of claim 1 wherein A is in the 7-position and R is a radioactive bromine or iodine isotope.
26. A dopamine receptor imaging agent of claim 25 where X is CH$_2$.
27. A dopamine receptor imaging agent of claim 25 where E is H.
28. A dopamine receptor imaging agent of claim 25 where D is N(propyl)((CH$_2$)$_n$CH=CHR.
29. A dopamine receptor imaging agent of claim 28 where X is CH$_2$ and E is H.
30. A serotonin 5-HT$_{1A}$ imaging agent comprising a compound of claim 1 wherein A is in the 8-position and R is a radioactive bromine or iodine isotope.
31. An imaging agent of claim 30 where X is CH$_2$.
32. An imaging agent of claim 30 where E is H.
33. An imaging agent of claim 30 where D is N(propyl)((CH$_2$)$_n$CH=CHR.
34. An imaging agent of claim 33 where X is CH$_2$ and E is H.
35. An imaging agent comprising a compound of claim 1 where R is a radioactive iodine or bromine isotope.
36. A method of imaging dopamine D-3 receptors in a patient comprising administering to said patient an effective quantity of the dopamine receptor imaging agent of claim 35 and measuring the gamma ray or photo emissions therefrom.

37. A method of imaging serotonin 5-HT$_{1A}$ receptors in a patient comprising administering to said patient an effective quantity of the dopamine receptor imaging agent of claim 35 and measuring the gamma ray or photo emissions therefrom.

38. The compound of claim 14 which is [$^{123}$I]-7-hydroxy-2-(N-n-propyl-N-3'-iodo-2'-propenyl)-amino-tetralin.

39. The compound of claim 17 which is [I$^{123}$I]-8-hydroxy-2-(N-n-propyl-N-3'-iodo-2'-propenyl)amino-tetralin.

40. A kit for preparing an imaging agent comprising a vial containing a physiologically suitable solution of a compound of claim 20 and a vial containing a radiohalogen and an oxidant.

41. A kit for preparing an imaging agent comprising a vial containing a physiologically suitable solution of claim 20 and a vial containing (i) a radioisotope selected from the group consisting of radioisotopes of iodine and bromine and (ii) hydrogen peroxide.

* * * * *

UNITED STATES PATENT AND TRADEMARK OFFICE
CERTIFICATE OF CORRECTION

PATENT NO. : 5,690,906
DATED : November 25, 1997
INVENTOR(S) : Kung

It is certified that error appears in the above-indentified patent and that said Letters Patent is hereby corrected as shown below:

In Column 18, line 18, delete "H-CH$_2$" and insert -- H$_2$-CH$_2$ -- therefor.

In Column 23, line 6, delete "7-OH-PIPAT" and insert -- 7-OH-DPAT -- therefor.

In Column 29, line 62 in the Claims, delete "where E is N" and insert -- where E is H -- therefor.

Signed and Sealed this

Seventh Day of April, 1998

Attest:

BRUCE LEHMAN

*Attesting Officer*   *Commissioner of Patents and Trademarks*